(12) United States Patent
Kovatchev et al.

(10) Patent No.: US 10,420,489 B2
(45) Date of Patent: Sep. 24, 2019

(54) SYSTEM COORDINATOR AND MODULAR ARCHITECTURE FOR OPEN-LOOP AND CLOSED-LOOP CONTROL OF DIABETES

(75) Inventors: Boris P. Kovatchev, Charlottesville, VA (US); Stephen D. Patek, Charlottesville, VA (US); Marc D. Breton, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1233 days.

(21) Appl. No.: 13/322,943

(22) PCT Filed: May 28, 2010

(86) PCT No.: PCT/US2010/036629
§ 371 (c)(1),
(2), (4) Date: Nov. 29, 2011

(87) PCT Pub. No.: WO2010/138848
PCT Pub. Date: Dec. 2, 2010

(65) Prior Publication Data
US 2012/0078067 A1 Mar. 29, 2012

Related U.S. Application Data

(60) Provisional application No. 61/182,454, filed on May 29, 2009.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/7275* (2013.01); *G16H 20/17* (2018.01); *G16H 50/20* (2018.01); *G16H 50/50* (2018.01)

(58) Field of Classification Search
CPC ..................... A61M 2230/201; A61B 5/14532
See application file for complete search history.

(56) References Cited

U.S. PATENT DOCUMENTS 6,544,212 B2 *  4/2003  Galley et al. ................. 604/31
6,923,763 B1    8/2005  Kovatchev et al.
(Continued)

FOREIGN PATENT DOCUMENTS

WO   01/13786 A1   3/2001
WO   01/72208 A2   10/2001
(Continued)

OTHER PUBLICATIONS

"Computer Architecture." http://www.thefreedictionary.com/computer+architecture. Retrieved Aug. 3, 2016.*
(Continued)

*Primary Examiner* — Meredith Weare
(74) *Attorney, Agent, or Firm* — Buchanan Ingersoll & Rooney PC

(57) ABSTRACT

A structure, method, and computer program product for a diabetes control system provides, but is not limited thereto, the following: open-loop or closed-loop control of diabetes that adapts to individual physiologic characteristics and to the behavioral profile of each person. An exemplary aspect to this adaptation is biosystem (patient or subject) observation and modular control. Consequently, established is the fundamental architecture and the principal components for a modular system, which may include algorithmic observers of patients' behavior and metabolic state, as well as interacting control modules responsible for basal rate, insulin boluses, and hypoglycemia prevention.

18 Claims, 5 Drawing Sheets

(51) Int. Cl.
  *G16H 50/50* (2018.01)
  *G16H 50/20* (2018.01)
  *G16H 20/17* (2018.01)

(56) References Cited

U.S. PATENT DOCUMENTS

| | | | |
|---|---|---|---|
| 7,025,425 B2 | 4/2006 | Kovatchev et al. | |
| 7,768,408 B2* | 8/2010 | Reggiardo | A61B 5/0002 340/573.1 |
| 7,806,886 B2* | 10/2010 | Kanderian et al. | 604/504 |
| 7,815,569 B2 | 10/2010 | Kovatchev et al. | |
| 7,874,985 B2 | 1/2011 | Kovatchev et al. | |
| 8,135,548 B2 | 3/2012 | Breton et al. | |
| 8,538,703 B2 | 9/2013 | Kovatchev et al. | |
| 8,585,593 B2 | 11/2013 | Kovatchev et al. | |
| 2003/0028089 A1* | 2/2003 | Galley et al. | 600/365 |
| 2004/0034295 A1 | 2/2004 | Salganicoff | |
| 2004/0193025 A1* | 9/2004 | Steil et al. | 600/316 |
| 2004/0254434 A1 | 12/2004 | Goodnow et al. | |
| 2005/0049179 A1 | 3/2005 | Davidson et al. | |
| 2005/0214892 A1 | 9/2005 | Kovatchev et al. | |
| 2006/0094947 A1 | 5/2006 | Kovatchev et al. | |
| 2006/0276771 A1* | 12/2006 | Galley et al. | 604/503 |
| 2007/0173761 A1* | 7/2007 | Kanderian et al. | 604/131 |
| 2008/0154513 A1 | 6/2008 | Kovatchev et al. | |
| 2008/0172205 A1 | 7/2008 | Breton et al. | |
| 2008/0183060 A1* | 7/2008 | Steil et al. | 600/365 |
| 2008/0287755 A1* | 11/2008 | Sass et al. | 600/309 |
| 2008/0300919 A1 | 12/2008 | Charlton et al. | |
| 2008/0314395 A1 | 12/2008 | Kovatchev et al. | |
| 2009/0006061 A1* | 1/2009 | Thukral et al. | 703/11 |
| 2009/0006129 A1* | 1/2009 | Thukral et al. | 705/2 |
| 2009/0006133 A1 | 1/2009 | Weinert et al. | |
| 2009/0069745 A1 | 3/2009 | Estes et al. | |
| 2009/0076358 A1* | 3/2009 | Reggiardo | A61B 5/0002 600/365 |
| 2009/0171589 A1 | 7/2009 | Kovatchev | |
| 2009/0221890 A1* | 9/2009 | Saffer et al. | 600/347 |
| 2010/0114015 A1* | 5/2010 | Kanderian et al. | 604/66 |
| 2010/0228111 A1* | 9/2010 | Friman | A61B 5/14532 600/365 |
| 2010/0249561 A1* | 9/2010 | Patek et al. | 600/365 |

FOREIGN PATENT DOCUMENTS

| | | |
|---|---|---|
| WO | 2004/015539 A2 | 2/2004 |
| WO | 2005/106017 A2 | 11/2005 |
| WO | 2007/027691 A1 | 3/2007 |
| WO | 2007/081853 A2 | 7/2007 |
| WO | 2008/052199 A2 | 5/2008 |
| WO | 2008/067284 A2 | 6/2008 |
| WO | 2008/157780 A1 | 12/2008 |
| WO | 2008/157781 A1 | 12/2008 |
| WO | 2009/009528 A2 | 1/2009 |
| WO | 2009/059187 A1 | 5/2009 |
| WO | 2010/062898 A1 | 6/2010 |
| WO | 2010/099313 A1 | 9/2010 |

OTHER PUBLICATIONS

Beck et al., "Outcome Measures for Outpatient Hypoglycemia Prevention Studies," Journal of Diabetes Science and Technology, (Jul. 2011), vol. 5, Issue 4, pp. 999-1004.

Bellazzi et al., "The Subcutaneous Route to Insulin-Dependent Diabetes Therapy," IEEE Engineering in Medicine and Biology, (Jan./Feb. 2001), vol. 20, No. 1, pp. 54-64.

Bergman et al., "Quantitative Estimation of Insulin Sensitivity," American Journal of Physiology, (Jun. 1979), vol. 236, Issue 6, pp. E667-E677.

Breton et al., "Adaptive Algorithm Predicting Hypoglycemia in Continuous Glucose Monitoring," University of Virginia, Charlottesville, VA, USA, pp. A14.

Breton et al., "Optimum Subcutaneous Glucose Sampling and Fourier Analysis of Continuous Glucose Monitors," Journal of Diabetes Science and Technology, (May 2008), vol. 2, Issue 3, pp. 495-500.

Breton et al., "Analysis, Modeling, and Simulation of the Accuracy of Continuous Glucose Sensors," Journal of Diabetes Science and Technology, (Sep. 2008), vol. 2, Issue 5, pp. 853-862.

Buckingham et al., "Preventing Hypoglycemia Using Predictive Alarm Algorithms and Insulin Pump Suspension," Diabetes Technology & Therapeutics, (2009), vol. 11, No. 2, pp. 93-97.

Chan et al., "Effects of Pulsatile Subcutaneous Injections of Insulin Lispro on Plasma Insulin Concentration Levels," Journal of Diabetes Science and Technology, (Sep. 2008), vol. 2, Issue 5, pp. 844-852.

Clarke et al., "Statistical Tools to Analyze Continuous Glucose Monitor Data," Diabetes Technology & Therapeutics, (Jun. 2009), vol. 11, Supplement 1, pp. S-45-S54.

Clarke et al., "Closed-Loop Artificial Pancreas Using Subcutaneous Glucose Sensing and Insulin Delivery and a Model Predictive Control Algorithm: The Virginia Experience," Journal of Diabetes Science and Technology, (Sep. 2009), vol. 3, Issue 5, pp. 1031-1038.

Clemens et al., "The Development of Biostator, a Glucose Controlled Insulin Infusion System (GCIIS)," Hormone and Metabolic Research, (1977), Suppl 7, pp. 23-33 (16 pages).

Cobelli et al., "Evaluation of Portal/Peripheral Route and of Algorithms for Insulin Delivery in the Closed-Loop Control of Glucose in Diabetes-A Modeling Study," IEEE Transactions on Biomedical Engineering, (Feb. 1983), vol. BME-30, No. 2, pp. 93-103.

Cryer, "Hypoglycaemia: The Limiting Factor in the Glycaemic Management of Type I and Tpye II Diabetes," Diabetologia, (Jul. 2002), vol. 45, No. 7, pp. 937-948.

Dalla Man et al., "GIM, Simulation Software of Meal Glucose-Insulin Model," Journal of Diabetes Science and Technology, (May 2007), vol. 1, Issue 3, pp. 323-330.

Dalla Man et al., "Meal Simulation Model of the Glucose-Insulin System," IEEE Transactions on Biomedical Engineering, (Oct. 2007), vol. 54, No. 10, pp. 1740-1749.

Danne et al., "Prevention of Hypoglycemia by Using Low Glucose Suspend Function in Sensor-Augmented Pump Therapy," Diabetes Technology & Therapeutics, (Nov. 2011), vol. 13, No. 11, pp. 1129-1134.

Dassau et al., "In Silico Evaluation Platform for Artificial Pancreatic β-Cell Development-A Dynamic Simulator for Closed-Loop Control with Hardware-in-the-Loop," Diabetes Technology & Therapeutics, (2009), vol. 11, No. 3, pp. 187-194.

Dassau et al., "Real-Time Hypoglycemia Prediction Suite Using Continuous Glucose Monitoring," Diabetes Care, (Jun. 2010), vol. 33, No. 6, pp. 1249-1254.

Dassau et al., "Modular Artificial β-Cell System: A Prototype for Clinical Research," Journal of Diabetes Science and Technology, (Sep. 2008), vol. 2, Issue 5, pp. 863-872.

Dua et al., "Model-Based Blood Glucose Control for Type 1 Diabetes via Parametric Programming," IEEE Transactions on Biomedical Engineering, (Aug. 2006), vol. 53, No. 8, pp. 1478-1491.

Hovorka, "Continuous Glucose Monitoring and Closed-Loop Systems," Diabetic Medicine, (Jan. 2006), vol. 23, No. 1, pp. 1-12.

Hovorka et al., "Nonlinear Model Predictive Control of Glucose Concentration in Subjects with Type 1 Diabetes," Physiological Measurement, (Aug. 2004), vol. 25, No. 4, pp. 905-920.

Hovorka, "The Future of Continuous Glucose Monitoring: Closed Loop," Current Diabetes Reviews, (Aug. 2008), vol. 4, No. 3, pp. 269-279.

King et al., "Modeling of Calibration Effectiveness and Blood-to-Interstitial Glucose Dynamics as Potential Confounders of the Accuracy of Continuous Glucose Sensors during Hyperinsulinemic Clamp," Journal of Diabetes Science and Technology, (May 2007), vol. 1, Issue 3, pp. 317-322.

Klonoff, "The Artificial Pancreas: How Sweet Engineering Will Solve Bitter Problems," Journal of Diabetes Science and Technology, (Jan. 2007), vol. 1, Issue 1, pp. 72-81.

(56) References Cited

OTHER PUBLICATIONS

Kovatchev et al., "Risk Analysis of Blood Glucose Data: A Quantitative Approach to Optimizing the Control of Insulin Dependent Diabetes," Journal of Theoretical Medicine, (Jan. 2000), vol. 3, Issue 1, pp. 1-10.
Kovatchev et al., "Association of Self-Monitoring Blood Glucose Profiles with Glycosylated Hemoglobin in Patients with Insulin-Dependent Diabetes," Methods in Enzymology, (2000), vol. 321, pp. 410-417.
Kovatchev et al., "Episodes of Severe Hypoglycemia in Type 1 Diabetes are Preceded and Followed within 48 Hours by Measurable Disturbances in Blood Glucose," The Journal of Clinical Endocrinology & Metabolism, (Nov. 2000), vol. 85, No. 11, pp. 4287-4292.
Kovatchev et al., "Algorithmic Evaluation of Metabolic Control and Risk of Severe Hypoglycemia in Type 1 and Type 2 Diabetes Using Self-Monitoring Blood Glucose Data," Diabetes Technology & Therapeutics, (2003), vol. 5, No. 5, pp. 817-828.
Kovatchev et al., "Quantifying Temporal Glucose Variability in Diabetes via Continuous Glucose Monitoring: Mathematical Methods and Clinical Application," Diabetes Technology & Therapeutics, (Dec. 2005), vol. 7, No. 6, pp. 849-862.
Kovatchev et al., "Personalized Subcutaneous Model-Predictive Closed-Loop Control of T1DM: Pilot Studies in the USA and Italy," Conference: Conference: 69th Annual Meeting of the American-Diabetes-Association, (Jun. 2009), vol. 58, pp. 1-2.
Kovatchev et al., "In Silico Model and Computer Simulation Environment Approximating the Human Glucose-Insulin Utilization," Food and Drug Administration Master File MAF 1521, (2008), (66 pages).
Kovatchev et al., "Peculiarities of the Continuous Glucose Monitoring Data Stream and Their Impact on Developing Closed-Loop Control Technology," Journal of Diabetes Science and Technology, (Jan. 2008), vol. 2, Issue 1, pp. 158-163.
Kovatchev et al., "In Silico Preclinical Trials: A Proof of Concept in Closed-Loop Control of Type 1 Diabetes," Journal of Diabetes Science and Technology, (Jan. 2009), vol. 3, Issue 1, pp. 44-55.
Kovatchev et al., "Comparison of the Numerical and Clinical Accuracy of Four Continuous Glucose Monitors," Diabetes Care, (Jun. 2008), vol. 31, No. 6, pp. 1160-1164.
Kovatchev et al., "Study of Closed-Loop Glucose Control in Type 1 Diabetes Based on Continuous Glucose Monitoring (CGM), Model-Predictive Control (MPC) Algorithm, and Manual Insulin Pump Regulation," Investigational Device Exemption (IDE) Application, (Mar. 2008), pp. 1-169.
Kovatchev et al., "Symmetrization of the Blood Glucose Measurement Scale and its Applications," Diabetes Care, (Nov. 1997), vol. 20, No. 11, pp. 1655-1658.
Kovatchev et al., "Assessment of Risk for Severe Hypoglycemia Among Adults with IDDM: Validation of the Low Blood Glucose Index," Diabetes Care, (Nov. 1998), vol. 21, No. 11, pp. 1870-1875.
Kovatchev et al., "Evaluation of a New Measure of Blood Glucose Variability in Diabetes," Diabetes Care, (Nov. 2006), vol. 29, No. 11, pp. 2433-2438.
Kovatchev et al., "Evaluating the Accuracy of Continuous Glucose-Monitoring Sensors Continuous glucose-error grid analysis illustrated by TheraSense Freestyle Navigator data," Diabetes Care, (Aug. 2004), vol. 27, No. 8, pp. 1922-1928.
Kovatchev et al., "Field Glucose Variability Index is Related to Laboratory Measures of Insulin Sensitivity and Hypoglycaemia Counterregulation," Diabetologia, (2006), vol. 49, Suppl. 1, pp. 537-538.
Magni et al., "Evaluating the Efficacy of Closed-Loop Glucose Regulation via Control-Variability Grid Analysis," Journal of Diabetes Science and Technology, (Jul. 2008), vol. 2, Issue 4, pp. 630-635.
Magni et al., "Model Predictive Control of Type 1 Diabetes: an in Silico Trial," Journal of Diabetes Science and Technology, (Nov. 2007), vol. 1, Issue 6, pp. 804-812.
McCall et al., "A Novel Analytical Method for Assessing Glucose Variability: Using CGMS in Type 1 Diabetes Mellitus," Diabetes Technology & Therapeutics, (Dec. 2006), vol. 8, No. 6, pp. 644-653.
Nathan et al., "The Effect of Intensive Treatment of Diabetes on the Development and Progression of Long-Term Complications in Insulin-Dependent Diabetes Mellitus," The New England Journal of Medicine, (Sep. 30, 1993), vol. 329, No. 14, pp. 977-986.
Nucci et al., "Models of Subcutaneous Insulin Kinetics. A Critical Review," Computer Methods and Programs in Biomedicine, (Jul. 2000), vol. 62, No. 3, pp. 249-257.
Owens et al., "Run-to-Run Control of Blood Glucose Concentrations for People With Type 1 Diabetes Mellitus," IEEE Transactions on Biomedical Engineering, (Jun. 2006), vol. 53, No. 6, pp. 996-1005.
Palerm et al., "Prandial Insulin Dosing Using Run-to-Run Control: Application of Clinical Data and Medical Expertise to Define a Suitable Performance Metric," Diabetes Care, (May 2007), vol. 30, No. 5, pp. 1131-1136.
Parker et al., "A Model-Based Algorithm for Blood Glucose Control in Type I Diabetic Patients," IEEE Transactions on Biomedical Engineering, (Feb. 1999), vol. 46, No. 2, pp. 148-157.
Patek et al., "In Silica Preclinical Trials: Methodology and Engineering Guide to Closed-Loop Control in Type 1 Diabetes Mellitus," Journal of Diabetes Science and Technology, (Mar. 2009), vol. 3, Issue 2, pp. 269-282.
Patek et al., "Adaptive Meal Detection Algorithm for Enhancing Closed-Loop Control in Type 1 Diabetes," University of Virginia, Charlottesville, Virginia, USA, pp. A139.
Patek et al., "Linear Quadratic Gaussian-Based Closed-Loop Control of Type 1 Diabetes," Journal of Diabetes Science and Technology, (Nov. 2007), vol. 1, Issue 6, pp. 834-841.
Pillonetto et al., "A New Dynamic Index of Insulin Sensitivity," IEEE Transactions on Biomedical Engineering, (Mar. 2006), vol. 53, No. 3, pp. 369-379.
Pitsillides et al., "Hypoglycemia Risk and Glucose Variability Indices Derived from Routine Self-Monitoring of Blood Glucose Are Related to Laboratory Measures of Insulin Sensitivity and Epinephrine Counterregulation," Diabetes Technology & Therapeutics, (2011), vol. 13, No. 1, pp. 11-17.
Sorensen, "A Physiologic Model of Glucose Metabolism in Man and its use to Design and Assess Improved Insulin Therapies for Diabetes," Massachusetts Institute of Technology, (Apr. 1985), pp. 1-556.
Sparacino et al., "Glucose Concentration can be Predicted Ahead in Time From Continuous Glucose Monitoring Sensor Time-Series," IEEE Transactions on Biomedical Engineering, (May 2007), vol. 54, No. 5, pp. 931-937.
Steil et al., "Feasibility of Automating Insulin Delivery for the Treatment of Type 1 Diabetes," Diabetes, (Dec. 2006), vol. 55, No. 12, pp. 3344-3350.
"Intensive blood-glucose control with sulphonylureas or insulin compared with conventional treatment and risk of complications in patients with type 2 diabetes (UKPDS 33). UK Prospective Diabetes Study (UKPDS) Group," The Lancet, (Sep. 12, 1998), vol. 352, No. 9131, pp. 837-853.
Weinzimer et al., "Fully Automated Closed-Loop Insulin Delivery Versus Semiautomated Hybrid Control in Pediatric Patients With Type 1 Diabetes Using an Artificial Pancreas," Diabetes Care, (May 2008), vol. 31, No. 5, pp. 934-939.
Wentholt et al., "A Critical Appraisal of the Continuous Glucose—Error Grid Analysis," Diabetes Care, (Aug. 2006), vol. 29, No. 8, pp. 1805-1811.
Zanderigo et al., "Glucose Prediction Algorithms from Continuous Monitoring Data: Assessment of Accuracy via continuous Glucose Error-Grid Analysis," Journal of Diabetes Science and Technology, (Sep. 2007), vol. 1, Issue 5, pp. 645-651.
Zecchin et al., "Physical Activity Measured by Physical Activity Monitoring System Correlates with Glucose Trends Reconstructed from Continuous Glucose Monitoring," Diabetes Technology & Therapeutics, (Oct. 2013), vol. 15, vol. 10, pp. 836-844.
Zisser et al., "Run-to-Run Control of Meal-Related Insulin Dosing," Diabetes Technology & Therapeutics, (Feb. 2005), vol. 7, No. 1, pp. 48-57.
European Communication dated Jan. 9, 2019, issued in EP 10781299.2.

* cited by examiner

SYSTEM COORDINATOR AND MODULAR ARCHITECTURE FOR OPEN-LOOP AND CLOSED-LOOP CONTROL OF DIABETES

CROSS-REFERENCES TO RELATED APPLICATIONS

The present application is a national stage filing of International Application No. PCT/US2010/036629, filed May 28, 2010, which claims priority under 35 U.S.C. § 119(e) from U.S. Provisional Application Ser. No. 61/182,454, filed May 29, 2009, entitled "System Coordinator and Modular Architecture for Open-Loop and Closed-Loop Control of Diabetes;" of which the disclosures are hereby incorporated by reference herein in their entirety.

This invention was made with government support under NIH RO1 DK 085623 awarded by the National Institutes of Health. The government has certain rights in the invention.

FIELD OF THE INVENTION

Some aspects of some embodiments of this invention are in the field of medical methods, systems, and computer program products related to managing the treatment of diabetic subjects, more particularly to glycemic analysis and control.

BACKGROUND OF THE INVENTION

People with diabetes face a life-long optimization problem: to maintain strict glycemic control without increasing their risk for hypoglycemia [13, 58, 59]. The engineering challenge related to this problem is to design algorithms using automated insulin delivery to exert optimal closed-loop control of glucose fluctuations. Since the early studies of continuous external glucose regulation (e.g., BioStator, [10]), two primary approaches have emerged: The use of classic proportional-Integral-derivative (PID) algorithms, and modern methods based on models of the human metabolism. The first studies using subcutaneous insulin delivery and continuous glucose monitoring (CGM) employed PID control [57,60]. Recently, model predictive control (MPC), received considerable attention [20, 21, 44, 50] due to its many clinical and engineering advantages.

BRIEF SUMMARY OF THE INVENTION

MPC is typically based on a model of the human metabolic system. Fortunately, the modeling of glucose-insulin interaction is one of the most advanced applications of mathematics to medicine. Beginning with the now classic Minimal Model of Glucose Kinetics (MMGK) co-authored by Dr. Claudio Cobelli who leads the Italian team of this project [2], a number of elaborate models have been developed [16,21]. These models can be classified in three broad classes: (i) models to measure parameters that are not accessible by direct lab tests, such as MMGK assessing insulin sensitivity; (ii) models to simulate that enable in silico pre-clinical trials, and (iii) models to control used to empower algorithms such as MPC.

An aspect of an embodiment of the present invention provides the progress towards advisory open-loop control or automated closed-loop control that will be greatly accelerated by a structured modular approach to building control components. Specifically, an aspect of an embodiment of the present invention provides a system of control modules responsible for basal rate, pre-meal and correction insulin boluses, and hypoglycemia prevention. These modules will be informed by biosystem observers providing information about the patients' glycemic state. A modular approach to closed-loop control development would have a number of advantages that include, but are not limited to:
  Incremental testing of modules in parallel or consecutive studies;
  Incremental FDA approval and industrial deployment of system features;
  User flexibility—each system observer or control module could be used separately, or within an integrated control system, depending on patients' or physicians' choice;

An aspect of an embodiment provides an external open-loop or closed-loop control that shall have separate interacting components responsible for prevention of hypoglycemia, postprandial insulin correction boluses, basal rate control, and administration of pre-meal boluses. These control modules receive information from biosystem observers that are responsible for tracking glucose fluctuations and the amount of active insulin at any point in time. This dual control-observer architecture is dictated by the natural separation of the computational elements of a closed-loop control system into algorithms observing the person and algorithms actuating control. Central role in this architecture is played by the system coordinator—an algorithmic module that is responsible for controlling the integration and the interactions of the modular system.

Pertaining to the feasibility of each of the proposed observers and control modules, as well as the feasibility of using CGM technology and subcutaneous insulin delivery for automated closed-loop control the following may be referenced:
  Use and accuracy of CGM; algorithmic processing of CGM data: [3, 5, 24, 26, 29, 34, 40];
  In silico pre-clinical trials: [15, 16, 28, 31];
  Glucose variability observer and Risk Analysis: [36, 37, 38, 39, 42, 43, 46];
  Insulin observer, subcutaneous insulin transport, sensitivity, and action: [0, 2, 7, 12, 47, 54];
  Control module 1: prediction and prevention of hypoglycemia: [4, 26, 35, 53, 56, 61];
  Control modules 2, 3, and 4: correction boluses and closed-loop control: [8, 11, 27, 44, 45, 51].

An embodiment of the present invention defines a modular architecture that can accommodate a variety of system observers and control modules that can be assembled into a system for open-loop advisory mode control or automated closed-loop control of diabetes.

An aspect of an embodiment of the present invention, a structure, method, and computer program product for a diabetes control system provides, but is not limited thereto, the following: open-loop or closed-loop control of diabetes that adapts to individual physiologic characteristics and to the behavioral profile of each person. An exemplary aspect to this adaptation is biosystem (patient) observation and modular control. Consequently, an aspect of an embodiment of the present invention establishes the fundamental architecture and the principal components for a modular system, which includes algorithmic observers of patients' behavior and metabolic state, as well as interacting control modules responsible for basal rate, insulin boluses, and hypoglycemia prevention. An exemplary role in this architecture is played by the system coordinator—such as an algorithmic module that may be responsible for controlling the integration and the interactions of the modular system.

An aspect of an embodiment of the present invention provides a structure, method, and computer program product for a diabetes control system provides, but is not limited thereto, the following: open-loop or closed-loop control of diabetes that adapts to individual physiologic characteristics and to the behavioral profile of each person. An exemplary aspect to this adaptation is biosystem (patient) observation and modular control. Consequently, an aspect of an embodiment of the present invention establishes the fundamental architecture and the principal components for a modular system, which may include algorithmic observers of patients' behavior and metabolic state, as well as interacting control modules responsible for basal rate, insulin boluses, and hypoglycemia prevention.

An aspect of an embodiment of the present invention provides a structure for a diabetes control system. The structure may comprise: modules for processing and storing data; conduits between modules; and signals produced in the event that certain modules are not inserted within the structure.

An aspect of an embodiment of the present invention provides a computer program product comprising a computer useable medium having a computer program logic for enabling at least one processor in a computer system for a diabetes control system. The computer program logic may be configured to include: modules for processing and storing data; conduit means between modules; and producing signals in the event that certain modules are not inserted within the system.

An aspect of an embodiment of the present invention provides a method for enabling a diabetes control system. The method may comprise: providing modules for processing and storing data; providing conduits or the like between modules; and producing signals in the event that certain modules are not inserted within the system.

These and other objects, along with advantages and features of various aspects of embodiments of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF THE INVENTION

Figure 1:
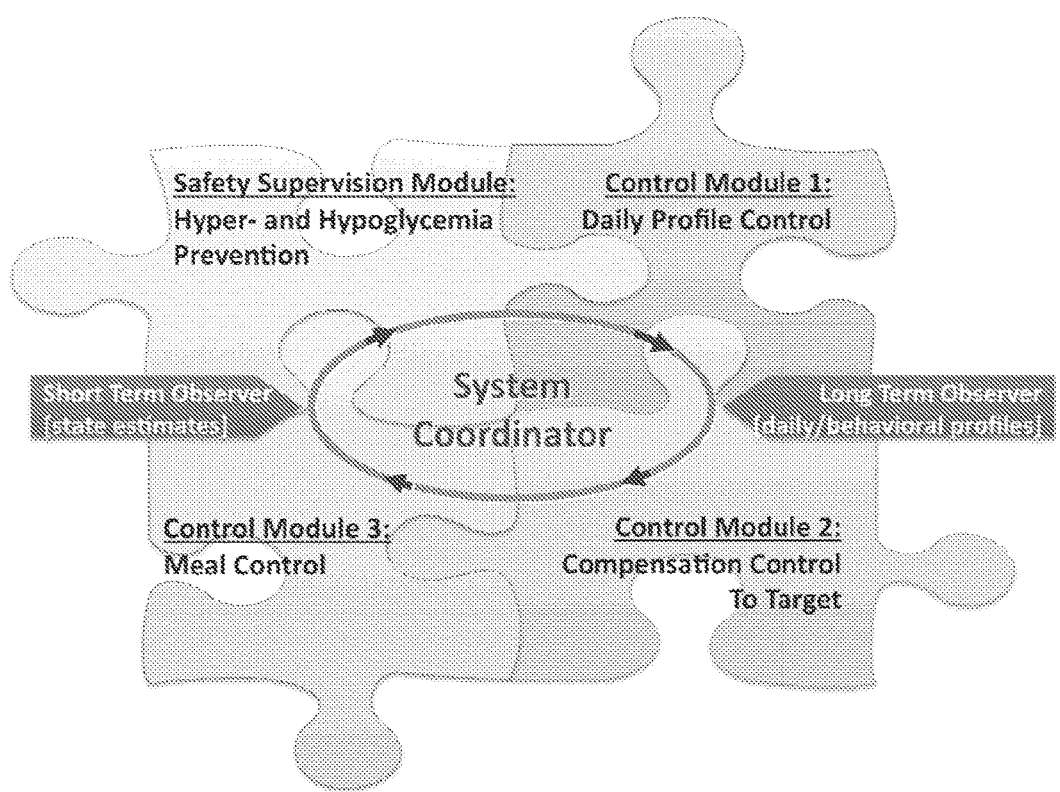
FIG. 1 schematically provides an exemplary embodiment of the structure of the modular architecture for control of diabetes.

Definitions
For the purposes of an embodiment of the present invention:
  Open-loop advisory-mode control is defined as a system that uses CGM data and information from insulin pump to provide real-time advice about treatment adjustments to patients with diabetes;
  Closed-loop control system is defined as a system using data from CGM devices and information from insulin pump to automatically control insulin delivery by the insulin pump.
Overview of Modular Architecture of Open-Loop and Closed-Loop Control of Diabetes:
  As shown in FIG. 1, a modular open- or closed-loop control system includes observers of patients' metabolic state, daily profiles and behavior, which provide information to the central system coordinator, which in turn directs the actions and the interactions of an array of control modules. Specifically:
  A System Coordinator will coordinate the distribution of input signals to control modules (routing) and most importantly allocate different segments of diabetes management to different controllers by restricting the input to these controllers (see example in discussion below). Finally, the system coordinator will ensure the direct feeding of external inputs to controllers if the observers are inactive.
  Observers will receive frequent information about metabolic measurements (such as continuous glucose or insulin), metabolic disturbances (such as meals or exercise), and metabolic treatments (such as insulin or glucagon injections). Based on these inputs the observers will
    construct and update an internal representation of the metabolic state of the patient and transmit this state to the control modules;
    keep an internal representation of the behavioral pattern of the patient, such as daily meal and exercise profiles; and
    assess risks for undesirable events such as hypoglycemia or glucose variability.
  Safety Supervision Module will receive information from the observers and from the control modules (below) and will decide whether there is an increase of the risk for upcoming hypoglycemia or prolonged hyperglycemia. If risk increase in encountered, the module will reduce or discontinue the suggested insulin infusion.
  Three Control Modules will be responsible for insulin administration. The Control Modules will receive instructions from the System Coordinator and will supply their output to the Safety Supervision Module for evaluation. The Control Modules are:
    Control Module 1 will calculate and suggest the basal insulin delivery;
    Control Module 2 will calculate and suggest compensation of the basal delivery (up or down) in case of non meal related deviations, such as drops or rise due to exercise, or residual dawn phenomenon not covered by module 1;
    Control Module 3 will calculate and suggest meal insulin boluses, potentially including pre-meal priming boluses.
  While the Safety Supervision Module and the Control Modules are subjects of independent invention disclosures or have been developed elsewhere [44,51], the subject of an embodiment the present invention is defining the general architecture of an open-loop or a closed-loop control system and the interactions between the components (modules) of that system as presented in FIGS. 1 and 2. A feature of an embodiment of the present invention is the design of the System Coordinator, responsible for the seamless integration of observers, control modules, and safety supervision.
  In the context of engineering design of an embodiment, it may be important to underscore that:

Each system observer or control module can be used separately, or within an integrated open- or closed-loop control system, depending on patients' or physicians' choice. This modular approach will allow the incremental testing of system features in parallel or consecutive studies;

The operation of the system in open-loop advisory mode will be conceptually similar to closed-loop control mode, but will differ in terms of implementation: open-loop will provide real-time information to the patient, while closed-loop will control directly the insulin pump.

Figure 2:
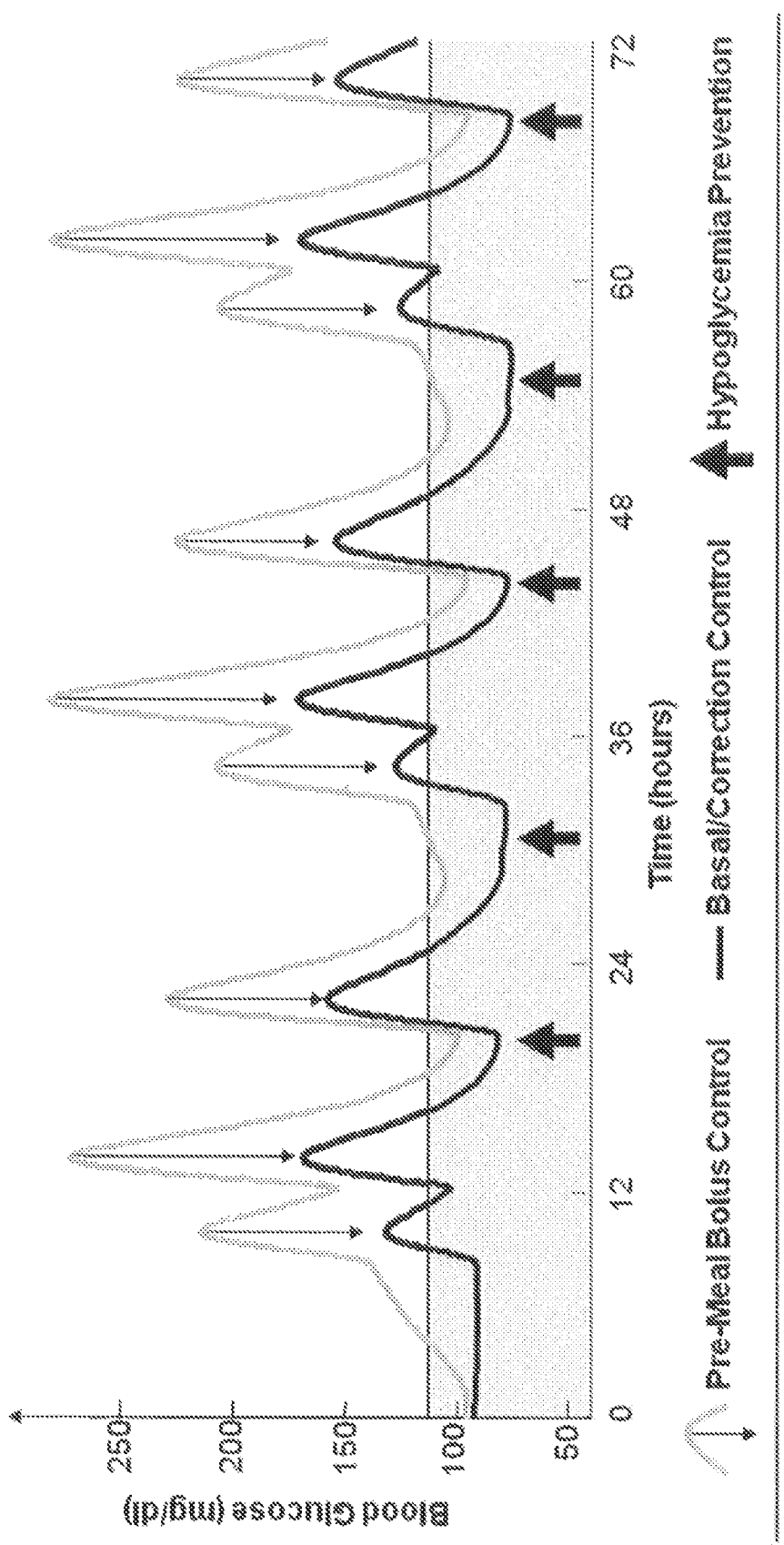
FIG. 2 schematically provides an exemplary decoupled basal and bolus control supervised by hypoglycemia prevention.

An exemplary idea behind the introduction of a System Coordinator is its ability to decouple different control functions, and to coordinate the control module action with separate modules responsible for different aspect of diabetes management, such as meals, exercise, basal pattern, and hypo/hyperglycemia avoidance. In other words, separate interacting algorithms will suggest optimal pre-meal bolus control (e.g. a stochastic algorithm) and will exercise basal rate control or administer post-meal correction boluses (e.g. deterministic algorithms). This "separation of duties" corresponds to the stochastic nature of meals and behavior, and the deterministic nature of basal and postprandial physiology, and also has deep mathematical reasoning motivated by the experience gained in our recent clinical trials of closed-loop control in Type 1 diabetes. These trials showed excellent overnight regulation but rather slow (as compared to open loop) breakfast regulation. Tuning of the algorithm aggressiveness alone was not sufficient to achieve both goals. It was therefore necessary to introduce a strategy that handles differently night and breakfast regulation. With this in mind, we introduce the System Coordinator, which allows each Control Module to operate within a certain BG range. Specifically, after Module 3 treats a meal, the effect of this bolus and the concurring meal is projected 1-2 h ahead and will be subtracting in real time from the trajectory from the incoming CGM data. In other words, the System Coordinator will "correct" the CGM track sent to Module 2 by the projected action of Module 3. This modus operandi is illustrated in FIG. 2: the observed glucose trace is presented by a gray line, but Module 2 will only "see" the black trace, which is the difference between real-time CGM and the action of Module 3. This will result in a rather simple interaction between Modules 1, 2 and 3: Module 1 sets the reference treatment for the day, Module 3 will operate in a regime with updates every several hours, its action will be continuously projected, and the result will be supplied to Module 2, which will operate in frequent increments (e.g. 15 minutes)

Further, all control modules will be supervised by the Safety Supervision module, which will warn the person for upcoming hypo/hyperglycemia and will suggest reduction in insulin delivery or correction boluses in open-loop advisory mode, or will directly reduce or discontinue the insulin pump infusion rate in closed-loop control mode.

Figure 3:
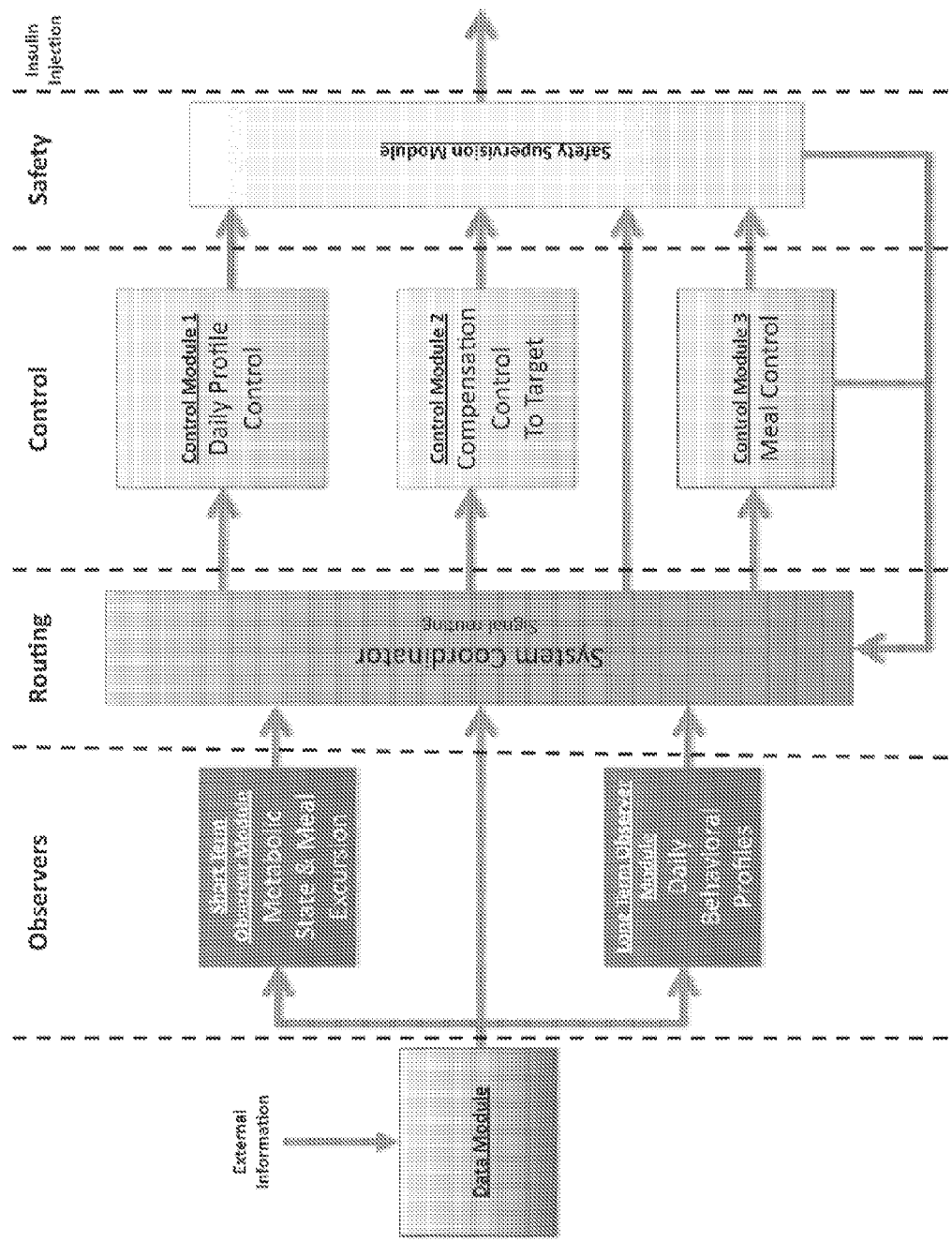
FIG. 3 schematically provides a first exemplary embodiment of the general architecture for control of diabetes.
Figure 4:
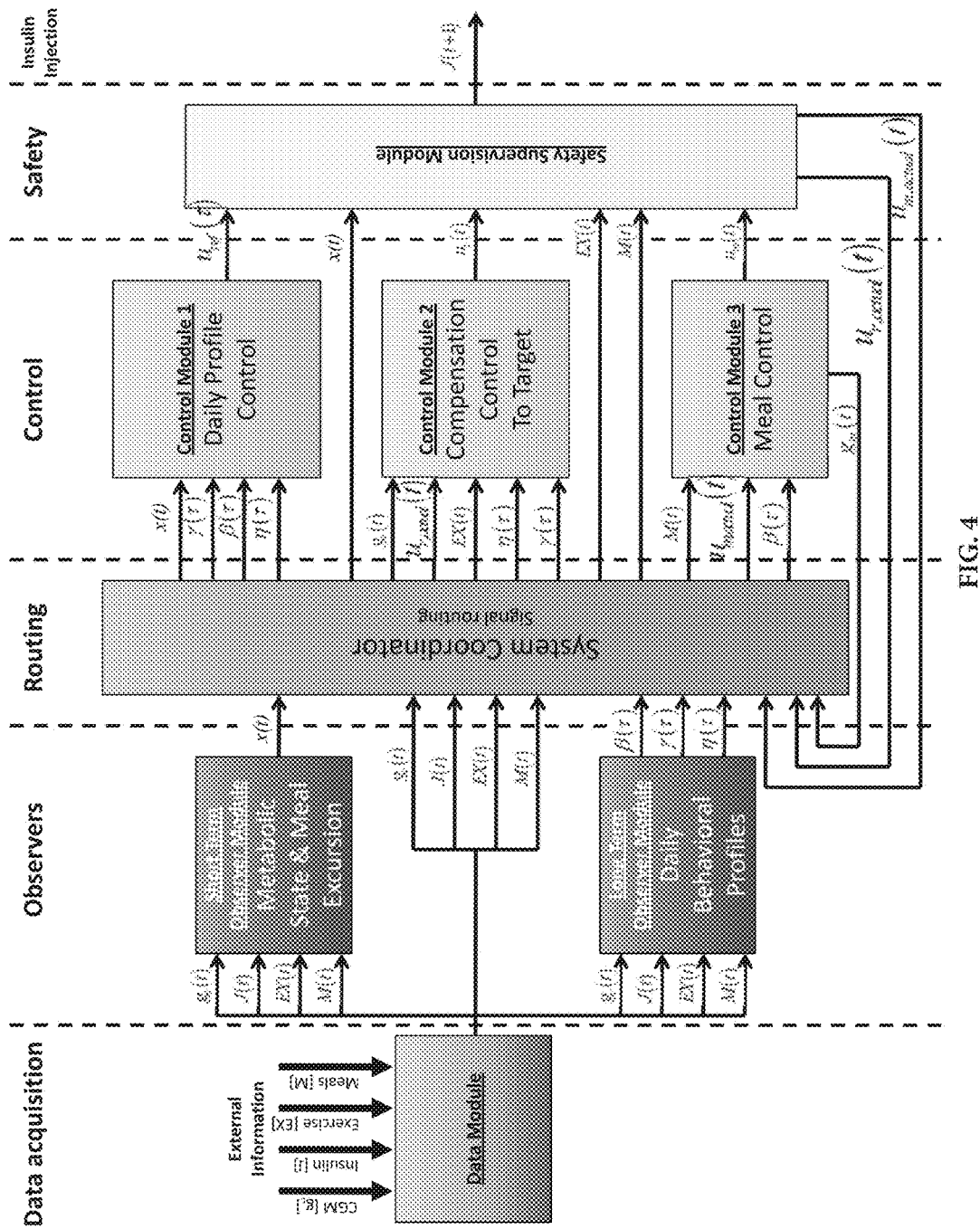
FIG. 4 schematically provides a detailed embodiment of the general architecture for control of diabetes.

FIG. 3 presents a flow chart of the interactions between the system components indentified in FIG. 1, while FIG. 4 presents a detailed view of the nodes and the conduits of the modular architecture, featuring the interactions of the System Coordinator with the other components of an open-loop advisory system or a closed-loop control system. The only difference between open-loop advisory operation and closed-loop control operation is in the delivery of information from the System Coordinator: in open-loop the information about insulin rate and potential for hypoglycemia is presented to the patient; in closed-loop control mode insulin delivery commands are send directly to the insulin pump. The following paragraphs describe the function of each of the modules of the architecture, focusing largely on the interfaces between modules and the requirements/definition of each signal. This description assumes that the system updates are computed in discrete time t, corresponding to given sampling interval. We use the terms "time," "discrete time," and "stage" interchangeably.

The Data Module serves to process raw data from external sources, scan the data for integrity, and produce four real-time signals that are then used by the remaining modules of the modular system. As shown in FIG. 4, the external data sources are (1) continuous glucose monitoring (CGM) data, possibly from multiple sensors, (2) data from the patient's insulin pump (i.e. insulin actually delivered to the patient), (3) exercise information (e.g. heart rate information and other indicators of physical activity), and (4) meal information (e.g. acknowledgements of meals as they arrive). Only the CGM and the insulin pump data are mandatory; exercise and meal information is optional and will be used only in certain embodiments of this invention. The outputs of the data module are:

$g_c(t)$=a single, processed glucose sample at stage t, reflecting the effect of all processing of the glucose sensors used as input J(t)=the most recent (relative to t) actual insulin pump command (mU/min) It should be noted that all insulin injections are expressed as rates of infusion, including boluses.

EX(t)=exercise process data at time t (EX is an optional time series that is specific to the embodiment of the modular architecture)

M(t)=meal data at stage t (M is an optional time series that is specific to the embodiment of the modular architecture)

The Long Term Observer Module serves to produce statistical profiles of the patient's meal and exercise behavior, $\beta$ and $\eta$ respectively, and a circadian profile the patient's daily insulin utilization $\gamma$, which are used by other control modules to set priors on parameter estimates and/or constraints on insulin action. The inputs to the Long Term Observer Module are all of the Data Module outputs shown in FIG. 4: $g_c(t)$, J(t), EX(t), and M(t). The outputs of the module are:

$\beta(\tau)$=a daily profile of the patient's meal behavior, where the notation ($\tau$) expresses the fact that the profile is used as a lookup table descriptive of the patients behavior as a function of time of day $\eta(\tau)$=a daily profile of the patient's exercise behavior, where again the notation ($\tau$) expresses the fact that the profile is used as a lookup table descriptive of the patients behavior as a function of time of day $\gamma(\tau)$=a daily (circadian) profile of the patient's utilization of insulin, where again the notation ($\tau$) expresses the fact that the profile is used as a lookup table descriptive of the patients behavior as a function of time of day All outputs of the Long Term Observer Module are optional—the entire Long-Term Observer would only exist in certain specific embodiments of the modular architecture. Some embodiments of the modular architecture will not include an active Long Term Observer; in these embodiments the outputs of the model take default values, $\beta^0(\tau) \eta^0(\tau)$ and $\gamma^0(\tau)$, which are not utilized by the remaining modules of the system.

In one embodiment of the Long Term Observer Module, the meal behavioral profile $\beta$ defines a probabilistic description of the patients eating behavior within given "meal regimes" throughout the day. Specifically, for each meal regime β would comprise the conditional probability of a meal arriving within the next sampling interval (within the meal's window of opportunity), given that the meal has not yet arrived:

$$p_k = \frac{f_k}{1 - F + \sum_{i=1}^{\bar{k}} f_i} \qquad (1)$$

where $f_k$ is the frequency with which the corresponding meal arrives in the k-th sampling interval of the current meal regime, 1-F is the probability with which the meal will not arrive within its window of opportunity, and $\bar{k}$ is the latest possible stage in which the meal could arrive. In this scheme it is historical information about meals M(t) that allows for the "observation" of the meal behavioral profile β(τ), expressed as conditional probabilities $p_k$. Note that if the meal time is known in advance within the j-th sampling interval, then $p_k$ will be zero for all k not equal to j, and $p_j=1$. This embodiment of the meal behavioral profile would allow for the administration of insulin in anticipation of meals, without compromising patient safety.

The Short Term Observer Module of FIGS. 3 and 4 serves to compute real-time estimates of key metabolic states for the patient, including possibly plasma insulin and glucose concentration, which are used by Control Modules 1-3 to perform various tasks. The Safety Supervisor, for example, may use metabolic state estimates to assess/predict the risk of out-of-range excursions in blood glucose (i.e. episodes of hypoglycemia or hyperglycemia).

The biometric values that comprise the "key" metabolic states are specific to the embodiment of the modular architecture. However, at least one of the states will be blood glucose concentration. We use $\tilde{x}(t)$ to denote the vector of true metabolic state values, reserving the first element of the vector $\tilde{x}_1(t)$ to be defined as blood glucose concentration. It is important to note that the true values of the metabolic states are unknown in general because they are not the same as the input signals $g_c(t)$, J(t), EX(t), and M(t). (For example, while plasma glucose and insulin cannot be measured in real time, values for these states can be estimated from $g_c(t)$, J(t), EX(t), and M(t).) We use $\hat{\tilde{x}}(t)$ to denote the corresponding vector of state estimates.

Thus, the inputs of the Short Term Observer Module are the same as the outputs of Data Module shown in FIG. 3: $g_c(t)$, J(t), EX(t), and M(t). The output of the Short Term Observer Module is:

$\hat{\tilde{x}}(t)$=a vector of estimates of the key metabolic states of the patient, including plasma glucose and plasma insulin.

In embodiments of the modular architecture where the Short Term Observer is not active, the default state estimate is simply a pass-through of the glucose sample:

$$\hat{\tilde{x}}^0(t) = g_c(t). \qquad (2)$$

Even though the composition of the vectors $\tilde{x}(t)$ and $\hat{\tilde{x}}(t)$ is specific to the embodiment, we can describe the basic framework for how state estimation is performed. We assume that the evolution of the state vector is described by a discrete-time, nonlinear dynamic model, generally expressed as:

$$\tilde{x}(t+1) = \tilde{F}(\tilde{x}(t), J(t), \omega_m(t), \omega_e(t)), \qquad (3)$$

where $\omega_m(t)$ and $\omega_e(t)$ are disturbance processes representing meals and exercise/physical activity. The nonlinear model could be a discrete-time realization of the oral glucose meal model [16], minimal models derived from the meal model, the Hovorka [21] or the Sorensen model [55], or another yet to be determined mathematical model of glucose-insulin-exercise dynamics. The state estimate $\hat{\tilde{x}}(t)$ is derived through a process of filtering (state "observations") based on the processed input data $g_c(t)$, J(t), EX(t), and M(t). The filtering process could be a direct application of Kalman filtering, extended Kalman filtering, or another yet to be determined statistical procedure that incorporates state observation as a key internal process. The state estimation process is driven in part by a model for the relationship between these signals and the underlying state vector, expressed as:

$$CGM(t) = \tilde{G}_{CGM}(\tilde{x}(t)) + v_{CGM}(t) \qquad (4)$$

$$M(t) = \tilde{G}_m(\omega_m(t)) + v_m(t) \qquad (5)$$

$$EX(t) = \tilde{G}_e(\omega_e(t)) + v_e(t), \qquad (6)$$

where (1) $\tilde{G}_{CGM}$, $\tilde{G}_m$, and $\tilde{G}_e$ describe the functional relationship between the subject's actual metabolic state $\tilde{x}(t)$ and CGM(t), the actual meal disturbance $\omega_m(t)$ and the meal signal $y_m(t)$, and the actual exercise/physical activity disturbance $\omega_e(t)$ and the exercise data signal $y_e(t)$, respectively and (2) $v_{CGM}(t)$, $v_m(t)$, and $v_e(t)$ are sensor noise processes.

The System Coordinator shown in FIG. 4 plays a central role in the modular architecture, serving (1) to act as a "router" for signals from and to the various Control Modules and (2) to decompose the estimate blood glucose concentration into parts attributable to (i) meals and the response to meals and (ii) all other disturbances (exercise and physical activity). The System Coordinator receives a specific set of signals from the various Control Modules, listed in the following paragraphs.

From the Data Module, the System Coordinator receives $g_c(t)$, J(t), EX(t), and M(t). From the Long Term Observer Module, the System Coordinator receives the behavioral profiles β(τ), η(τ), and γ(τ), and, from the Short Term Observer Module, the System Coordinator receives the metabolic state vector estimate $\hat{\tilde{x}}(t)$. In addition, from the Safety Supervision Module, the System Coordinator receives:

$u_{m,actual}(t)$=insulin allowed at time t by the Safety Supervisor as a part of the response to meals $u_{r,actual}(t)$=insulin allowed at time t by the Safety Supervisor as a part of the response to non-meal disturbances From the Meal Control Module (Control Module 3), the Coordinator Receives $g_m(t)$=estimated glucose excursion due to meals (and the response to meals)

Many of the inputs to the System Coordinator are "passed through" to other control modules, as shown in FIG. 3.

In addition to acting as a "router" for signals between various modules, the System Coordinator play a central role in attributing glucose excursions to either (1) meals and the response to meals or (2) other metabolic disturbances. Specifically, the System Coordinator serves to evaluate $g_r(t)$=an estimate of blood glucose concentration offset by the estimated contribution of meals (and the response to meals), computed as $$g_r(t) = \hat{\tilde{x}}_1(t) - g_m(t) \qquad (7)$$

The signal $g_r(t)$ is the only output of the System Coordinator that is not a pass-through signal from other modules.

(Note that since output $g_m(t)$ of the Controller defaults to zero if the Meal Control Module is not active, then $g_r(t)$ is exactly the estimated value of blood glucose $\tilde{x}_1(t)$.)

The Daily Profile Control Module (Control Module 1) of FIG. 4 serves to compute a reference insulin signal $u_{ref}(t)$, which is analogous to the patient's daily insulin profile in conventional CSII therapy. The inputs to the Daily Profile Control Module are the outputs of the system observers: (1) the metabolic state vector estimate $\hat{x}(t)$ (produced by the Short Term Observer Module) and (2) the behavioral profiles $\beta(\tau)$, $\eta(i)$, and $\gamma(\tau)$ (produced by the Long Term Observer Module). The output of Daily Profile Control Module is:

$u_{ref}(t)$=reference insulin infused at time t

The computation of the reference insulin signal is specific to the embodiment of the modular architecture. In an embodiment where the Daily Profile Control Module is inactive, the default output is simply the patient's daily basal insulin profile.

The Meal Control Module (Control Module 3) of FIG. 4 serves to manage BG excursions in anticipation of and in response to meals in a quasi open-loop fashion. It does this by (1) maintaining an open-loop internal estimate of the contribution of meals to the patient's overall BG and (2) using the patient meal behavioral profile to compute recommended meal insulin $u_m(t)$ both prior to the meal arriving and after the meal. The inputs to the Meal Controller are M(t)=the meal data process (from the Data Module)

$U_{m,actual}(t)$=insulin allowed at time t by the Safety Supervisor as a part of the response to meals (produced by Safety Supervision Module)

$\beta(\tau)$=the meal behavioral profile (produced by the Long Term Observer Module)

The outputs of the Meal Controller (originating within the Meal Controller) are $u_m(t)$=the recommended insulin infusion at time t for accommodating meals $g_m(t)$=estimated glucose excursion due to meals (and the response to meals)

The computation of $u_m(t)$ and $g_m(t)$ are both specific to the embodiment of the modular architecture. In an embodiment where the meal control module is inactive, the recommended insulin infusion $u_m(t)$ defaults to zero, as does $g_m(t)$ the estimated glucose excursion due to meals, leaving the Compensation Control to Target Module (if active) to reject the meal disturbance.

For embodiments in which the Meal Control Module is active, estimation of the glucose excursion due to meals would be computed from an open loop dynamic system model, reflective of the dynamic interactions between glucose and insulin. Whatever dynamic system model is used can generally be described as a nonlinear discrete-time system, with state vector $\xi(t)$, whose evolution is dictated by:

$$\xi(t+1) = F_m(\xi(t), u_{m,actual}(t), M(t)). \qquad (8)$$

where the state space equations defined by the operator $F_m$ are such that, if $u_{m,actual}(t)$ is fixed at zero and M(t) is also fixed at zero, then $\xi(t)$ converges to zero asymptotically. The estimated excursion in blood glucose can be derived from the model as $$g_m(t) = G_m(\xi(t)). \qquad (9)$$

The same dynamic system model could be used in conjunction with the meal behavioral profile $\beta(\tau)$ to compute an optimal open loop response to meals, perhaps even in anticipate of meal arrival.

In one embodiment of the modular architecture with an active Meal Control Module, the behavioral profile $\beta(\tau)$ could express as the conditional probability $p_k$ of the meal arriving at stage k of the current meal regime (given that it has not already arrived). Such a meal behavioral profile would allow, the administration of insulin in anticipation of meals, without compromising patient safety. In this embodiment, the suggested meal control signal would be computed as a function of the control relevant statistics $y_m(t)$ and future conditional probabilities $p_t$, $p_{t+1}$, K, $p_{\bar{k}}$ as $$u_m(t) C_m(\xi(t), M(t), p_t, p_{t+1} K p_{\bar{k}}), \qquad (10)$$

where $C_m$ denotes the mathematical transformation of input data to optimal anticipatory and reactive insulin injections.

The Compensation Control to Target Module of FIG. 4 (Control Module 2) serves to manage in-range excursions of blood glucose that are not already accounted for by the Meal Control Module (Control Module 3). In serving in this capacity, this module maintains an internal estimate of the patient's "residual" metabolic state based on (1) the meal-offset glucose signal $g_r(t)$ produced by the System Coordinator, past residual insulin injections $u_{r,actual}(t)$ allowed by the Safety Supervisor, the exercise data process EX(t), and the exercise behavioral and insulin utilization profiles $\xi(\tau)$ and $\gamma(\tau)$.

The inputs to the Compensation Controller are $g_r(t)$=an estimate of glucose excursions away from $g_{ref}(t)$ that are not due to meals (computed by the System Coordinator)

$U_{r,actual}(t)$=insulin allowed at time t by the Safety Supervisor (computed by the Safety Supervisor)

EX(t)=the exercise data process from the Data Module)

$\eta$=exercise behavioral profile (produced by the Long Term Observer Module)

$\gamma$=circadian insulin profile (produced by the Long Term Observer Module)

The output of the Compensation Controller is $u_r(t)$=the recommended "residual" insulin infusion at time t needed to compensate for non-meal disturbances The computation of $u_r(t)$ is specific to the embodiment of the modular architecture. In an embodiment where the Compensation Control to Target Module is inactive, the default is $u_r(t)$=0. In this case the Safety Supervision Module (in conjunction with the Daily Profile Control Module and Meal Control Module) would take full responsibility for keeping the patient within an acceptable range of BG values.

In an embodiment of the modular architecture with an active Compensation Control to Target Module, the recommended residual insulin could be computed using Proportional-Integral-Derivative (PID) control, as in [57], using $e(t)=g_r(t)-g_{ref}(t)$ as an error signal, where $g_{ref}(t)$ is a possibly time-varying target.

In other embodiments of the modular architecture (in which the Compensation Control to Target Module is Active), the recommended residual insulin signal could be computed from a dynamic model of the interactions of $g_r(t)$ and residual insulin, which in general terms could be described as:

$$x(t+1) = F_r(x(t), u_{r,actual})(t), \omega_e(t)), \qquad (11)$$

where the state space equations defined by the operator $F_r$ are such that, if $u_{r,actual}(t)$ is fixed at zero and the exercise disturbance is also fixed at zero (i.e. no physical activity), then x(t) converges to a given target value $g_{ref}$ asymptotically. A vector of state estimates X(t) can be derived (through a process of state observation) using measurement models $$g_r(t)=G_r(x(t)) \quad (12)$$

$$EX(t)=G_e(\omega_e(t))+v_e(t), \quad (13)$$

The recommended residual control signal $u_r(t)$ is computed based on an estimate $\hat{x}(t)$ of the state vector $x(t)$ that is computed from the residual glucose signal $g_r(t)$. In one embodiment of the modular architecture, recommended residual control signal would be computed using closed-loop model predictive control techniques, as in [44] based on the estimate $\hat{x}(t)$. In other embodiments, Compensation Control could be achieved via LQG [51], LMPC, or any other closed loop control methodology. In yet other embodiments, compensation control could be achieve via either positive or negative residual "boluses", whose timing and extent are computed based on $\hat{x}(t)$.

The Safety Supervision Module of FIG. 4 monitors and, if necessary, modifies the suggested insulin injection signals produced by the other control modules, in an effort to (1) avoid hypoglycemia and (2) if the other modules are unable to do so, mitigate sustained hyperglycemia. In addition, the safety supervisor is responsible for computing the final "approved" next insulin injection $J(t+1)$ used as the main output of the modular architecture, attributing relevant parts of this signal to an "actual" meal control signal $u_{m,\,actual}(t)$ and an actual residual control signal $u_{r,actual}(t)$.

The inputs to the Safety Supervisor are $\hat{x}(t)$=the vector of estimated metabolic states for the patient, the first component of which, $\hat{x}_1(t)$, is an estimate of the patients blood glucose concentration (Short Term Observer Module)

$M(t)$=the meal data process (from the Data Module)

$EX(t)$=the exercise data process (form the Data Module)

$u_{ref}(t)$=reference insulin infused at time t (produced by the Daily Profile Control Module (Control Module 1))

$u_m(t)$=the recommended insulin infusion at time t for accommodating meals (produced by the Meal Control Module (Control Module 3))

$u_r(t)$=the recommended residual insulin infusion at time t for accommodating non-meal disturbances (produced by the Compensation Control to Target Module (Control Module 2))

The outputs of the Safety Supervisor (all generated by the Safety Supervisor) are $u_{m,actual}(t)$=insulin allowed at time t by the Safety Supervisor as a part of the response to meals $u_{r,actual}(t)$=insulin allowed at time t by the Safety Supervisor as a part of the response to non-meal disturbances $J(t+1)$=total insulin infusion allowed by the Safety Supervisor at time t The computation of $J(t+1)$ and the decomposition of $J(t+1)$ into actual meal and residual components is specific to the embodiment of the modular architecture. It is a requirement, however, that all of approved insulin must be account for as reference, meal, and residual insulin:

$$J(t+1)=u_{ref}(t)+u_{m,actual}(t)+u_{r,actual}(t) \quad (14)$$

In one embodiment of the modular architecture, the computation of $J(t+1)$ would be based on the prediction of future metabolic states $\hat{x}(t+\tau|t)$, given the current estimate $\hat{x}(t)$ of the metabolic state vector, the exercise data process $EX(t)$, and the suggested insulin amounts $u_{ref}(t)$, $u_m(t)$, and $u_r(t)$ held fixed at their current values:

$$\hat{x}(t+\tau|t)=\Phi_\tau(\hat{x}(t),EX(t),u_{ref}(t),u_m(t),u_r(t)). \quad (15)$$

The predicted future metabolic states $\hat{x}(t+\tau|t)$ would be factored into an assessment of the risk of hypoglycemia $\hat{R}(t+\tau|t)$ using the risk symmetrization procedure of [36,43]. In this embodiment, the total insulin control signal would be computed from the suggested values as $$J(t+1)=\frac{u_{ref}(t)+u_m(t)+u_r(t)}{1+k\cdot\hat{R}(t+\tau|t)} \quad (16)$$

where k is an aggressiveness factor for the attenuating function of the module, which would be determined from patient characteristics, such as body weight, total daily insulin, carb ratio, etc. The difference between $J(t)$ and $u_{ref}(t)+u_m(t)+u_r(t)$ would be attributed to $u_{m,actual}(t)+u_{r,\,actual}(t)$ according to a proportionality constant, $\alpha$ in $[0,1]$, as follows:

$$u_{m,actual}(t)=\alpha\cdot(J(t+1)-u_{ref}(t)) \quad (17)$$

$$u_{r,actual}(t)=(1-\alpha)\cdot(J(t+1)-u_{ref}(t)) \quad (18)$$

Note that if the risk $\hat{R}(t+\tau|t)$ of hypoglycemia is zero (which would be the case when predicted BG is greater than 112.5 mg/dl), then $J(t+1)=u_{ref}(t)+u_m(t)+u_r(t)$, $u_{m,actual}(t)=u_m(t)$, and $u_{r,actual}(t)=u_r(t)$.

An analogous computation could be used to compute a total approved insulin $J(t)$ to mitigate hyperglycemia, attributing the difference to $u_{m,actual}(t)$ and $u_{r,actual}(t)$.

Figure 5:
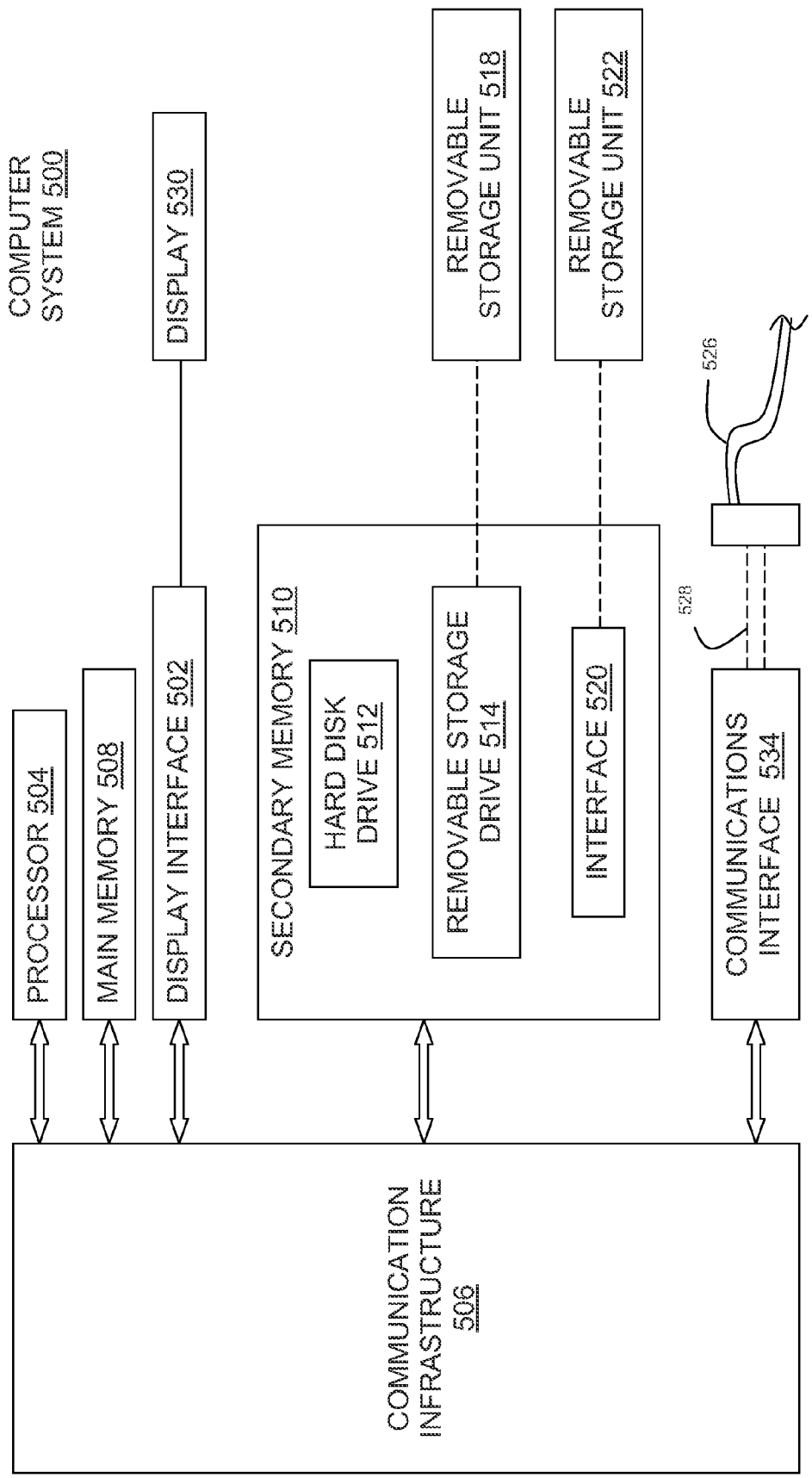
FIG. 5 schematically provides an exemplary embodiment of the general architecture for control of diabetes.

Turning to FIG. 5, FIG. 5 is a functional block diagram for a computer system 500 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 500 as illustrated in FIG. 5. The computer system 500 may includes one or more processors, such as processor 504. The Processor 504 is connected to a communication infrastructure 506 (e.g., a communications bus, cross-over bar, or network). The computer system 500 may include a display interface 502 that forwards graphics, text, and/or other data from the communication infrastructure 506 (or from a frame buffer not shown) for display on the display unit 530. Display unit 530 may be digital and/or analog.

The computer system 500 may also include a main memory 508, preferably random access memory (RAM), and may also include a secondary memory 510. The secondary memory 510 may include, for example, a hard disk drive 512 and/or a removable storage drive 514, representing a floppy disk drive, a magnetic tape drive, an optical disk drive, a flash memory, etc. The removable storage drive 514 reads from and/or writes to a removable storage unit 518 in a well known manner. Removable storage unit 518, represents a floppy disk, magnetic tape, optical disk, etc. which is read by and written to by removable storage drive 514. As will be appreciated, the removable storage unit 518 includes a computer usable storage medium having stored therein computer software and/or data.

In alternative embodiments, secondary memory 510 may include other means for allowing computer programs or other instructions to be loaded into computer system 500. Such means may include, for example, a removable storage unit 522 and an interface 520. Examples of such removable storage units/interfaces include a program cartridge and cartridge interface (such as that found in video game devices), a removable memory chip (such as a ROM, PROM, EPROM or EEPROM) and associated socket, and other removable storage units 522 and interfaces 520 which allow software and data to be transferred from the removable storage unit 522 to computer system 500.

The computer system 500 may also include a communications interface 524. Communications interface 124 allows software and data to be transferred between computer system 500 and external devices. Examples of communications interface 524 may include a modem, a network interface (such as an Ethernet card), a communications port (e.g., serial or parallel, etc.), a PCMCIA slot and card, a modem, etc. Software and data transferred via communications interface 524 are in the form of signals 528 which may be electronic, electromagnetic, optical or other signals capable of being received by communications interface 524. Signals 528 are provided to communications interface 524 via a communications path (i.e., channel) 526. Channel 526 (or any other communication means or channel disclosed herein) carries signals 528 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 514, a hard disk installed in hard disk drive 512, and signals 528. These computer program products ("computer program medium" and "computer usable medium") are means for providing software to computer system 500. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 508 and/or secondary memory 510. Computer programs may also be received via communications interface 524. Such computer programs, when executed, enable computer system 500 to perform the features of the present invention as discussed herein. In particular, the computer programs, when executed, enable processor 504 to perform the functions of the present invention. Accordingly, such computer programs represent controllers of computer system 500.

In an embodiment where the invention is implemented using software, the software may be stored in a computer program product and loaded into computer system 500 using removable storage drive 514, hard drive 512 or communications interface 524. The control logic (software or computer program logic), when executed by the processor 504, causes the processor 504 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

An embodiment of the present invention provides for, but not limited thereto, the development of an open-loop advisory system assisting patients with diabetes in the control of their blood glucose level, or a closed-loop control system (known as artificial pancreas) controlling automatically blood glucose. Accordingly, an aspect may provide, but not limited thereto, a complex project involving the development and the implementation of multiple mathematical algorithms, methods and engineering solutions.

Some aspects of an embodiment of the present invention diabetes control system, method and computer program product provides, but not limited thereto, the following: open-loop or closed-loop control must adapt to individual physiologic characteristics and to fast changing environmental factors; and keys to this adaptation are biosystem (patient) observation and modular control. Consequently, an aspect of an embodiment of the present invention diabetes control system, method and computer program product establishes the foundation for a modular system comprised of algorithmic observers of patients' behavior and metabolic state, and control modules responsible for insulin delivery and hypoglycemia prevention.

A component of such a modular system is the System Coordinator, which integrates the action of observers, control, and safety modules in order to:

In open-loop advisory mode, advise the patient about changes in basal rate, need for insulin boluses, or need to discontinue insulin delivery and take a preventive action due to increased risk for hypoglycemia.

In closed-loop control mode, command directly the insulin pump and issue warning for impending hypoglycemia to the patient if insulin pump shut-off would be insufficient to eliminate that risk.

Moreover, an embodiment of the present invention includes a modular approach enabled by a System Coordinator that will permit incremental testing and deployment of system features—observers and control modules—which will structure and facilitate system development.

Existing open- and closed-loop control algorithms do not include modular architecture—typically a single control module is implemented and charged with the function of delivering insulin regardless of the causes of glucose fluctuation. A modular approach enabled by a System Coordinator of an embodiment of the present invention allows the distribution of control and safety functions among specialized control modules that are then integrated by the System Coordinator.

A modular architecture of open-loop advisory system or closed-loop control system and method has many advantages, including but not limited to: the possibility of incremental development, testing, and deployment of control modules, and the possibility of using existing modules for incorporation in the system. Centralizing the system integration and coordination functions into a System Coordinator alleviates the separate control modules from the need of working in regimes that are unsuitable for their design. For example, a deterministic MPC is poorly suited to account for the stochastic nature of carbohydrate intake during meals, while a stochastic impulse control is poorly suited for maintaining a steady basal rate. Employing a System Coordinator permits different types of specialized algorithms to function together, each within the realm of its optimal performance.

The Modular Architecture and the System Coordinator included in an embodiment of the invention is suitable for implementation in open-loop advisory systems or closed-loop control systems for diabetes. These systems would typically use a continuous glucose monitor and an insulin pump, linked by the System Coordinator to optimize glucose control in diabetes. Other sources of information (e.g. heart rate monitoring that enables the recognition of exercise) can be included in the system as well, as long as interface with the System Coordinator is established.

It should be appreciated that as discussed herein, a subject may be a human or applicable in principle to animals. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

EXAMPLES

Practice of an aspect of an embodiment (or embodiments) of the invention will be still more fully understood from the following examples, which are presented herein for illustration only and should not be construed as limiting the invention in any way.

An aspect of an embodiment of the present invention provides a structure, system, or method for a diabetes control system. An embodiment of the structure or related method may comprise: modules for processing and storing data; conduits (or the like) between modules; and signals produced in the event that certain modules are not inserted within the structure. The structure may comprise different implementations of modules that can be inserted and/or interchanged. The modules for processing and storing data may be configured to include one or more of the following: one or more data acquisition modules; one or more observer modules; one or more routing modules; one or more control modules; and one or more safety modules. The structure may further comprise an insulin injector for injecting insulin based on the output of the one or more safety modules. One or more of the data acquisition modules may receive one or more of the following types of information: continuous glucose monitoring data; insulin pump data; exercise data; and meal data. The exercise data may include heart rate information, motion sensor information, and other indicators of physical activity. The meal data may include acknowledgements of meals as they arrive.

The one or more data acquisition modules may be configured to output one or more of the following types of information: a single, processed glucose sample at a specific time, or a history of glucose samples up to a specific time, or a statistic computed from glucose samples up to a specific time; a most recent actual insulin pump command, or a history of recent insulin pump commands up to a specific time, or a statistic computed from recent commands; exercise process data at the specific time; and meal data at the specific time. The one or more observer modules may be configured to receive one or more of the following types of information: a single, processed glucose sample at a specific time, or a history of glucose samples up to a specific time, or a statistic computed from glucose samples up to a specific time; a most recent actual insulin pump command, or a history of recent insulin pump commands up to a specific time, or a statistic computed from recent commands; exercise process data at the specific time; and meal data at the specific time. The one or more observer modules may be configured to process one or more of the following: metabolic measurements; metabolic disturbances; and metabolic treatments.

The metabolic measurements may include one or more of the following: continuous glucose measurements; and insulin measurements. The metabolic disturbances may include one or more of the following: meals; and exercise. The metabolic treatments may include one or more of the following: insulin injections; other pharmaceuticals (hormones) associated with the management of diabetes; treatments for hypoglycemia; and glucagon injections. The other pharmaceuticals may include hormones. The treatments for hypoglycemia may include administering rescue carbohydrates and/or glucagon injections.

The one or more observer modules may be configured to construct and update an internal representation or estimate of a metabolic state of an individual. The one or more observer modules may be configured to transmit metabolic state information to the one or more control modules. The one or more observer modules may be configured to keep an internal representation of a behavioral pattern of an individual. The one or more observer modules may be configured to assess risks of undesirable events. The one or more observer modules may include a short term observer module. The short term observer module may contain information relating to: metabolic state; meal excursion; and/or metabolic state and meal excursion. The short term observer module observes X times per hour, where X is 0<X<7200. It should be appreciated that the frequency may be greater or less as desired or required. The short term observer module may be configured to output one of the following: a vector of estimates of key metabolic states of an individual; a single, processed glucose sample at a specific time, or a history of glucose samples up to a specific time, or a statistic computed from glucose samples up to a specific time; or both the vector of estimates of key metabolic states and the sample or history of processed glucose samples. The vector of estimates may include plasma glucose and plasma insulin.

The one or more observer modules may include a long term observer module. The long term observer module may contain information relating to behavioral profiles. The behavioral profiles may be daily behavioral profiles, but may vary as desired or required. The long term observer module may assess behavioral profiles X times per month, where X is 0<X<60. It should be appreciated that the frequency may be greater or less as desired or required. The long term observer module may be configured to output one or more of the following types of information: a daily profile of an individual's meal behavior as a function of the time of day; a daily profile of the individual's exercise behavior as a function of the time of day; and a daily profile of the individual's utilization of insulin as a function of the time of day. The daily profile of the individual's meal behavior as a function of the time of day may include probabilities of eating at various times throughout the day and/or probabilities of taking various meals defined by carbohydrate, protein, and fat content. The daily profile of the individual's exercise behavior as a function of the time of day may include probabilities of various levels of physical activity throughout the day. The daily profile of the individual's utilization of insulin as a function of the time of day may include a trend analysis for meal and correction boluses and/or a trend analysis for basal rate profiles. The daily profile of an individual's meal behavior may define a probabilistic description of the individual's eating behavior within given meal regimes throughout a day. The behavioral data may be used to define a patient's breakfast regime and then assessing the probability of taking breakfast at any specific point of time within that regime.

The one or more routing modules may include a system coordinator. The system coordinator may be configured to coordinate the distribution of input signals to control one or more modules and allocate different segments of diabetes management to different control modules. The system coordinator may be configured to receive one or more of the following types of information: a single, processed glucose sample at a specific time, or a history of glucose samples up to a specific time, or a statistic computed from glucose samples up to a specific time; a most recent actual insulin pump command, or a history of recent insulin pump commands up to a specific time, or a statistic computed from recent commands; exercise process data at the specific time; meal data at the specific time; a vector of estimates of key metabolic states of an individual; a daily profile of an individual's meal behavior as a function of the time of day; a daily profile of the individual's exercise behavior as a function of the time of day; a daily profile of the individual's utilization of insulin as a function of the time of day; insulin allowed at the specific time by the one or more safety modules as part of a response to meals; insulin allowed at the specific time by the one or more safety modules as part of a response to non-meal disturbances; and estimated glucose excursion due to meals. The system coordinator may be configured to output one or more of the following types of information: a most recent actual insulin pump command; exercise process data at the specific time; meal data at the specific time; a vector of estimates of key metabolic states of an individual; a daily profile of an individual's meal behavior as a function of the time of day; a daily profile of the individual's exercise behavior as a function of the time of day; a daily profile of the individual's utilization of insulin as a function of the time of day; insulin allowed at the specific time by the one or more safety modules as part of a response to meals; insulin allowed at the specific time by the one or more safety modules as part of a response to non-meal disturbances; estimated glucose excursion due to meals; and an estimate of blood glucose concentration offset by the estimated contribution of meals.

The one or more control modules may be configured to perform: daily profile control; compensation control to target; and/or meal control. The daily profile control may include determining a basal rate baseline setting throughout the day, or some other period as desired or required. The compensation control to target may include small adjustments to the basal rate baseline to correct hyperglycemia and reduce the likelihood of hypoglycemia. The meal control may include a schedule of meal insulin following acknowledgement of a particular meal.

The one or more control modules may be configured to include: a first control module to calculate and suggest a basal insulin delivery; a second control module to calculate and suggest compensation of the basal delivery in case of non-meal-related deviations; and a third control module to calculate and suggest meal insulin boluses. The first control module may be configured to receive one or more of the following types of information: a vector of estimates of key metabolic states of an individual; a daily profile of an individual's meal behavior as a function of the time of day; a daily profile of the individual's exercise behavior as a function of the time of day; and a daily profile of the individual's utilization of insulin as a function of the time of day. The first control module may be configured to output a reference insulin infused at a specific time. The second control module may be configured to receive one or more of the following types of information: an estimate of blood glucose concentration offset by the estimated contribution of meals; insulin allowed at the specific time by the one or more safety modules as part of a response to non-meal disturbances; exercise process data at the specific time; a daily profile of the individual's exercise behavior as a function of the time of day; and a daily profile of the individual's utilization of insulin as a function of the time of day. The second control module may be configured to output a recommended residual insulin infusion at a specific time to compensate for non-meal-related disturbances. The third control module may be configured to receive one or more of the following types of information: meal data at the specific time; insulin allowed at the specific time by the one or more safety modules as part of a response to meals; and a daily profile of an individual's meal behavior as a function of the time of day. The third control module may be configured to output one or more of the following types of information: a recommended insulin infusion at a specific time for accommodating meals; and estimated glucose excursion due to meals. The second control module may compensate for a basal delivery up or down. The third control module may be configured to further calculate and suggests pre-meal priming boluses. Moreover, the first control module may operate approximately daily. It should be appreciated that the frequency may be greater or less as desired or required. The second control modules may operate approximately every fifteen to thirty minutes. It should be appreciated that the frequency may be greater or less as desired or required. The third control module may operate approximately every several hours. It should be appreciated that the frequency may be greater or less as desired or required.

The one or more safety modules may be configured to include a system supervision module. The system supervision module may be configured to receive one or more of the following types of information: exercise process data at the specific time; meal data at the specific time; a vector of estimates of key metabolic states of an individual; reference insulin infused at a specific time; a recommended insulin infusion at a specific time for accommodating meals; and a recommended residual insulin infusion at a specific time to compensate for non-meal-related disturbances. The system supervision module may be configured to output one or more of the following types of information: insulin allowed at a specific time by the one or more safety modules as part of a response to meals; insulin allowed at the specific time by the one or more safety modules as part of a response to non-meal disturbances; and total insulin infusion allowed by the safety supervision module at the specific time. The safety supervision module may be configured to: receive information from the one or more observer modules and one or more control modules; determine whether there is an increased risk of hypoglycemia or hyperglycemia; if it is determined that there is an increased risk of hypoglycemia, automatically reduce or discontinue a suggested infusion; and if it is determined that there is an increased risk of hyperglycemia, automatically notify the user of the risk. The increased risk of hypoglycemia may be defined as an increased risk of upcoming hypoglycemia or an increased risk of prolonged hypoglycemia. The suggested infusion may be an insulin infusion or a glucagon infusion. The safety supervision module may further comprise a display device for displaying real-time information to an individual. The individual may be a subject or a doctor, or other user as desired or required. The real-time information may include one or more of the following: a warning of hypoglycemia; a warning of hyperglycemia; a suggestion to reduce insulin delivery; and a suggestion to reject or reduce pre-meal or correction boluses.

Unless defined otherwise, all technical terms used herein have the same meanings as commonly understood by one of ordinary skill in the art of treating diabetes. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology. Further, while some theoretical considerations have been advanced in furtherance of providing an understanding, for example, of the quantitative interrelationships among carbohydrate consumption, glucose levels, and insulin levels, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Recited Publications

The following patents, applications and publications as listed below and throughout this document are hereby incorporated by reference in their entirety herein.

1. Bellazzi R, Nucci G, Cobelli C: The subcutaneous route to insulin-dependent diabetes therapy: closed-loop and partially closed-loop control strategies for insulin delivery and measuring glucose concentration. *IEEE Eng Med Biol* 20: 54-64, 2001.
2. Bergman R N, Ider Y Z, Bowden C R, Cobelli C. Quantitative estimation of insulin sensitivity. *Am J Physiol.* 236:E667-E677, 1979.
3. Breton M, Kovatchev B P. Analysis, modeling, and simulation of the accuracy of continuous glucose sensors. *J Diabetes Sci Technol* 2: 853-862, 2008.
4. Breton M D, Kovatchev B P, Facchinetti A, Patek S D, Cobelli C. Adaptive Algorithm Predicting Hypoglycemia in Continuous Glucose Monitoring (CGM) Data. Proc. 7$^{th}$ *Diabetes Technology Meeting*, San Francisco, Calif., 2007.

5. Breton M D, Shields D P, and Kovatchev B P (2008). Optimum Subcutaneous Glucose Sampling and Fourier-Analysis of Continuous Glucose Monitors. *J Diabetes Sci Technol*, 2: 495-500.
6. Buckingham B, Corby E, Clinton P, et al. Preventing Hypoglycemia Using Predictive Alarm Algorithms and Insulin Pump Suspension, *Diabetes Technol Ther*, 11:93-97, 2009.
7. Chan A, Breton M D and Kovatchev B P. Effects of pulsatile subcutaneous injections of insulin lispro on plasma insulin concentration levels. *J Diabetes Sci Technol*, 2: 844-852, 2008
8. Clarke W L and Kovatchev B P. The Artificial Pancreas: How Close We Are to Closing the Loop? *Ped Endocrinol Rev*, 4: 314-316, 2007
9. Clarke W L and Kovatchev B P. Statistical Tools to Analyze Continuous Glucose Monitoring Data, *Diabetes Technol Ther* (in press—Appendix 3).
10. Clemens A H, Chang P H, Myers R W. The development of Biostator, a glucose-controlled insulin infusion system. *Horm Metab Res Supplement*, 7: 23-33, 1977.
11. Cobelli C and Kovatchev B P. Clinical trial of model-predictive control powered by in silico studies. *Proc. 2$^{nd}$ Advanced Technology & Treatment for Diabetes*, Athens, Greece, 2009.
12. Cobelli C, Ruggeri A: Evaluation of portal/peripheral route and of algorithms for insulin delivery in the closed-loop control of glucose in diabetes. A modeling study. *IEEE Trans Biomed Eng* 30: 93-103, 1983.
13. Cryer P E. Hypoglycaemia: The limiting factor in the glycaemic management of type I and type II diabetes. *Diabetologia* 45: 937-948, 2002.
14. Dalla Man C, Breton M D, Cobelli C. Physical Activity into the Meal Glucose-Insulin Model of Type 1 Diabetes: In Silico Studies. *J Diabetes Sci Technol*, 3:56-67, 2009.
15. Dalla Man C, Raimondo D M, Rizza R A, and Cobelli C (2007). GIM, Simulation Software of Meal Glucose-Insulin Model. *J Diabetes Science and Technology*, 1: 323-330.
16. Dalla Man C, Rizza R A, and Cobelli C (2007). Meal simulation model of the glucose-insulin system. *IEEE Trans Biomed Eng*, 54:1740-1749.
17. Dassau E, Palerm C C, Zisser H, Buckingham B A, Jovanovič L and F J Doyle III. In silico benchmark platform for artificial pancreatic b-cell development—a dynamic simulator for closed-loop control with hardware-in-the-loop. *Diabetes Technol Ther* 11, 2009
18. Dassau E, Zisser H, Palerm C C, Buckingham B A, Jovanovič L, Doye III F J. Modular Artificial β-Cell System: A Prototype for Clinical Research *J Diabetes Sci Technol*. 2008; 2:863-872.
19. Dassau E., Cameron F., Lee H., Bequette B. W., Doyle III F. J., Günter N., Chase H. P. and Buckingham B. A. (2008). "Real-time Hypoglycemia Prediction Using Continuous Glucose Monitoring (CGM), A Safety Net to the Artificial Pancreas". Diabetes 57 (Supl 1): A13. *Proc of the 68th American Diabetes Association Meeting*, San Francisco Calif., USA.
20. Dua P, Doyle F J 3rd, Pistikopoulos E N. "Model-Based Blood Glucose Control for Type 1 Diabetes via Parametric Programming." *IEEE Trans Biomed Eng*. 53:1478-1491, 2006.
21. Hovorka R, Canonico V, Chassin L J, et al. Nonlinear model predictive control of glucose concentration in subjects with type 1 diabetes. *Physiol Meas* 25:905-920, 2004.
22. Hovorka R. The future of continuous glucose monitoring: closed loop. *Curr Diabetes Rev* 4: 269-79, 2008
23. Hovorka R: Continuous glucose monitoring and closed-loop systems. *Diabet Med* 23:1-12, 2006.
24. King C R, Anderson S M, Breton M D, Clarke W L, Kovatchev B P: Modeling of calibration effectiveness and blood-to-interstitial glucose dynamics as potential confounders of the accuracy of continuous glucose sensors during hyperinsulinemic clamp. *J Diabetes Sci Technol*, 2007, 1:317-322.
25. Klonoff D C: The Artificial Pancreas: How Sweet Engineering Will Solve Bitter Problems. *J Diabetes Sci Technol*, 1: 72-81, 2007.
26. Kovatchev B P and Clarke W L. Peculiarities of the Continuous Glucose Monitoring Data Stream and Their Impact on Developing Closed-Loop Control Technology. *J Diabetes Sci Technol*, 2:158-163, 2008.
27. Kovatchev B P et al. Personalized subcutaneous model—predictive closed—loop control of T1DM: Pilot studies in the USA and Italy, *Proc 69$^{th}$ ADA Scientific Session*, 228-OR (in press—Appendix 2).
28. Kovatchev B P et al. Study of Closed-Loop Glucose Control in Type 1 Diabetes. Food and Drug Administration Investigational Device Exemption G080048, 2008.
29. Kovatchev B P, Anderson S M, Heinemann L, Clarke W L. Comparison of the numerical and clinical accuracy of four continuous glucose monitors. *Diabetes Care*, 31: 1160-1164, 2008
30. Kovatchev B P, Anderson S M, Otto E. Field Glucose Variability Index is Related to Laboratory Measures of Insulin Sensitivity and Hypoglycemia Counterregulation. *Diabetologia*, 49, Supplement 1: A855, 2005.
31. Kovatchev B P, Breton M D, Dalla Man C, Cobelli C. In Silico Preclinical Trials: A Proof of Concept in Closed-Loop Control of Type 1 Diabetes. *J Diabetes Sci Technol* 3: 44-55, 2009.
32. Kovatchev B P, Breton M D, Dalla Man C, Cobelli C. In Silico model and computer simulation environment approximating the human glucose/insulin utilization. Food and Drug Administration Master File MAF 1521, 2008.
33. Kovatchev B P, Breton M D, Dalla Man C, Cobelli C. In Silico Preclinical Trials: A Proof of Concept in Closed-Loop Control of Type 1 Diabetes. *J Diabetes Sci Technol*, 2009, 3:44-55.
34. Kovatchev B P, Clarke W L, Breton M, Brayman K, McCall A. Quantifying Temporal Glucose Variability in Diabetes via Continuous Glucose Monitoring: Mathematical Methods and Clinical Application. *Diabetes Tech Ther*, 7: 849-862, 2005.
35. Kovatchev B P, Cox D J, Farhy L S, Straume M, Gonder-Frederick L A, Clarke, W L. Episodes of Severe Hypoglycemia in Type 1 Diabetes are Preceded, and Followed, within 48 Hours by Measurable Disturbances in Blood Glucose. *J of Clinical Endocrinology and Metabolism*, 85: 4287-4292, 2000.
36. Kovatchev B P, Cox D J, Gonder-Frederick L A and W L Clarke. Symmetrization of the blood glucose measurement scale and its applications. *Diabetes Care* 20: 1655-1658, 1997
37. Kovatchev B P, Cox D J, Gonder-Frederick L A Young-Hyman D, Schlundt D, Clarke W L. Assessment of risk for severe hypoglycemia among adults with IDDM: Validation of the Low Blood Glucose Index, *Diabetes Care* 21: 1870-1875, 1998.
38. Kovatchev B P, Cox D J, Kumar A, Gonder-Frederick L A and W L Clarke. Algorithmic Evaluation of Metabolic Control and Risk of Severe Hypoglycemia in Type 1 and Type 2 Diabetes Using Self-Monitoring Blood Glucose (SMBG) Data. *Diabetes Technol Ther*, 5: 817-828, 2003

39. Kovatchev B P, Cox D J, Straume M, Farhy L S. Association of Self-monitoring Blood Glucose Profiles with Glycosylated Hemoglobin (2000). *In: Methods in Enzymology, vol. 321: Numerical Computer Methods, Part C:* 410-417 M. Johnson & L. Brand, Eds., Academic Press, NY.

40. Kovatchev B P, Gonder-Frederick L A, Cox D J, Clarke W L: Evaluating the accuracy of continuous glucose monitoring sensors: Continuous Glucose Error-Grid Analysis (CG-EGA) illustrated by Therasense Freestyle Navigator™ data. *Diabetes Care* 27:1922-1928, 2004.

41. Kovatchev B P, Hovorka R, Weinzimer S for the JDRF Artificial Pancreas Consortium. Outcome measures: Judging the effectiveness of closed-loop control. JDRF AP Consortium Position Paper.

42. Kovatchev B P, Otto E, Cox D J, Gonder-Frederick L A, Clarke W L. Evaluation of a New Measure of Blood Glucose Variability in Diabetes. Diabetes Care, 29: 2433-2438, 2006.

43. Kovatchev B P, Straume M, Cox D J, Farhy L S. Risk analysis of blood glucose data: A quantitative approach to optimizing the control of insulin dependent diabetes. *J of Theoretical Medicine*, 3:1-10, 2001.

44. Magni L, Raimondo F, Bossi L, Dalla Man C, De Nicolao G, Kovatchev B P, Cobelli C. Model Predictive Control of Type 1 Diabetes: An In Silico Trial *J Diabetes Sci Technol*, 1: 804-812, 2007

45. Magni L, Raimondo F, Dalla Man C, Breton M D, Patek S, De Nicolao G, Cobelli C, and Kovatchev B P. Evaluating the Efficacy of Closed-Loop Glucose Regulation via Control-Variability Grid Analysis. *J Diabetes Sci Technol*, 2: 630-635, 2008

46. McCall A, Cox D J, Crean J, Gloster M, and Kovatchev B P. A Novel Analytical Method for Assessing Glucose Variability: Using CGMS in Type 1 Diabetes Mellitus. *Diabetes Technology and Therapeutics*, 8: 644-653, 2006.

47. Nucci G., Cobelli C. Models of subcutaneous insulin kinetics. A critical review. Comput Methods Programs Biomed., 62:249-57 Review, 2000.

48. Owens C, Zisser H, Jovanovic L, Srinivasan B, Bonvin D, Doyle F J 3rd. Run-to-run control of blood glucose concentrations for people with Type 1 diabetes mellitus. *IEEE Trans Biomed Eng*. 53:996-1005, 2006

49. Palerm C C, Zisser H, Bevier W C, Jovanovic L, Doyle F J 3rd. Prandial insulin dosing using run-to-run control: application of clinical data and medical expertise to define a suitable performance metric. *Diabetes Care*. 30:1131-1136, 2007

50. Parker R S, Doyle F J 3rd, Peppas N A. A model-based algorithm for blood glucose control in Type I diabetic patients. *IEEE Trans Biomed Eng*, 48:148-157, 1999.

51. Patek S D, Breton M D, Chen Y, Solomon C, and Kovatchev B P. LQG-Based Closed-Loop Control of Type 1 Diabetes. *J Diabetes Sci Technol*, 1: 834-841, 2007.

52. Patek S D, Breton M D, Cobelli C, Dalla Man C, and Kovatchev B P. Adaptive Meal Detection Algorithm Enabling Closed-Loop Control in Type 1 Diabetes. Proc. 7*th* *Diabetes Technology Meeting*, San Francisco, Calif., 2007.

53. Patek S D, Breton M D, Hughes C, and Kovatchev B P. Control of Hypoglycemia via Estimation of Active Insulin, Glucose Forecasts, and Risk-Based Insulin Reduction. *Proc. 2nd Advanced Technology & Treatment for Diabetes*, Athens, Greece, 2009.

54. Pillonetto G, Caumo A, Sparacino G, Cobelli C. A new dynamic index of insulin sensitivity. *IEEE Transactions on Biomedical Engineering*. 53: 369-79, 2006.

55. Sorensen J T: A Physiologic Model of Glucose Metabolism in Man and its Use to Design and Assess Improved Insulin Therapies for Diabetes, Ph.D. dissertation, Dept Chemical Engineering, MIT, 1985.

56. Sparacino G, Zanderigo F, Corazza G, Maran A, Facchinetti A, Cobelli C. Glucose concentration can be predicted ahead in time from continuous glucose monitoring sensor time-series. *IEEE Trans. Biomed Eng*, 54:931-937, 2007

57. Steil G M, Rebrin K, Darwin C, Hariri F, Saad M F. Feasibility of automating insulin delivery for the treatment of type 1 diabetes. *Diabetes* 55: 3344-3350, 2006.

58. The Diabetes Control and Complications Trial Research Group. The effect of intensive treatment of diabetes on the development and progression of long-term complications of insulin-dependent diabetes mellitus. *N Engl J Med* 329: 978-986, 1993.

59. UK Prospective Diabetes Study Group (UKPDS). Intensive blood-glucose control with sulphonylureas or insulin compared with conventional treatment and risk of complications in patients with type 2 diabetes. *Lancet* 352: 837-853, 1998.

60. Weinzimer S A, Steil G M, Swan K L, Dziura J, Kurtz N, Tamborlane W V: Fully automated closed-loop insulin delivery versus semi-automated hybrid control in pediatric patients with type 1 diabetes using an artificial pancreas. *Diabetes Care* 31:934-939, 2008.

61. Zanderigo F, Sparacino G, Kovatchev B, Cobelli C. Glucose Prediction Algorithms from continuous monitoring: Assessment of accuracy via Continuous Glucose-Error Grid Analysis. *J Diabetes Sci Technol*, 1: 645-651, 2007

62. Zisser H, Jovanovic L, Doyle F J 3rd, Ospina P, Owens C. Run-to-Run Control of Meal-Related Insulin Dosing. *Diab Technol Ther*. 7:48-57, 2005

REFERENCES

The devices, structures, systems, computer program products, and methods of various embodiments of the invention disclosed herein may utilize aspects disclosed in the following references, applications, publications and patents and which are hereby incorporated by reference herein in their entirety:

A. International Patent Application Serial No. PCT/US2010/025405, entitled "Method, System and Computer Program Product for CGM-Based Prevention of Hypoglycemia via Hypoglycemia Risk Assessment and Smooth Reduction Insulin Delivery," filed Feb. 25, 2010

B. International Patent Application Serial No. PCT/US2009/065725, filed Nov. 24, 2009, entitled "Method, System, and Computer Program Product for Tracking of Blood Glucose Variability in Diabetes from Data,"

C. PCT/US2008/082063, entitled "Model Predictive Control Based Method for Closed-Loop Control of Insulin Delivery in Diabetes Using Continuous Glucose Sensing", filed Oct. 31, 2008.

D. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008.

E. PCT/US2008/067725, entitled "Method, System and Computer Simulation Environment for Testing of Monitoring and Control Strategies in Diabetes," filed Jun. 20, 2008.

F. PCT/US2008/067723, entitled "LQG Artificial Pancreas Control System and Related Method", filed on Jun. 20, 2008.

G. U.S. Ser. No. 12/516,044, filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes;"

H. PCT/US2007/085588 not yet published filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes;"

I. U.S. Ser. No. 11/943,226, filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes;"

J. U.S. patent application Ser. No. 11/578,831, filed Oct. 18, 2006 entitled "Method, System and Computer Program Product for Evaluating the Accuracy of Blood Glucose Monitoring Sensors/Devices".

K. PCT International Application Serial No. PCT/US2005/013792, filed Apr. 21, 2005, entitled "Method, System, and Computer Program Product for Evaluation of the Accuracy of Blood Glucose Monitoring Sensors/Devices;"

L. PCT International Application Serial No. PCT/US01/09884, filed Mar. 29, 2001, entitled "Method, System, and Computer Program Product for Evaluation of Glycemic Control in Diabetes Self-Monitoring Data;"

M. U.S. Pat. No. 7,025,425 B2 issued Apr. 11, 2006, entitled "Method, System, and Computer Program Product for the Evaluation of Glycemic Control in Diabetes from Self-Monitoring Data;"

N. U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 2006/0094947);

O. PCT International Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"

P. U.S. patent application Ser. No. 10/524,094 filed Feb. 9, 2005 entitled "Managing and Processing Self-Monitoring Blood Glucose" (Publication No. 2005/214892);

Q. U.S. Ser. No. 12/065,257, filed Aug. 29, 2008, entitled "Accuracy of Continuous Glucose Sensors;"

R. PCT International Application Serial No PCT/US2006/033724, filed Aug. 29, 2006, entitled "Method for Improvising Accuracy of Continuous Glucose Sensors and a Continuous Glucose Sensor Using the Same;"

S. U.S. Ser. No. 12/159,891, filed Jul. 2, 2008, entitled "Method, System and Computer Program Product for Evaluation of Blood Glucose Variability in Diabetes from Self-Monitoring Data;"

T. PCT International Application No. PCT/US2007/000370, filed Jan. 5, 2007, entitled "Method, System and Computer Program Product for Evaluation of Blood Glucose Variability in Diabetes from Self-Monitoring Data;"

U. U.S. patent application Ser. No. 11/925,689 and PCT International Patent Application No. PCT/US2007/082744, both filed Oct. 26, 2007, entitled "For Method, System and Computer Program Product for Real-Time Detection of Sensitivity Decline in Analyte Sensors;"

V. U.S. Ser. No. 10/069,674, filed Feb. 22, 2002, entitled "Method and Apparatus for Predicting the Risk of Hypoglycemia;"

W. PCT International Application No. PCT/US00/22886, filed Aug. 21, 2000, entitled "Method and Apparatus for Predicting the Risk of Hypoglycemia;"

X. U.S. Pat. No. 6,923,763 B1, issued Aug. 2, 2005, entitled "Method and Apparatus for Predicting the Risk of Hypoglycemia;"

Y. U.S. Patent Application No. US 2004/0254434 A1, "Glucose Measuring Module and "Insulin Pump Combination", Dec. 16, 2004.

Z. U.S. Patent Application Publication No. US 2009/00697456 A1, Estes, et al., "Operating an Infusion Pump System", Mar. 12, 2009.

What is claimed is:

1. An apparatus having a modular architecture for managing diabetes of a patient, comprising:

a system coordinator controller device configured to receive metabolic measurement data and metabolic state estimate data of the patient and to selectively route this data to a selected number of activated controller devices selectively activated by the system coordinator controller device for particularized diabetes management of a specific patient;

the selectively activated controller devices including:

a daily profile controller device configured to compute a reference insulin infusion signal in response to at least a metabolic state estimate of the patient, a meal controller device configured to compute a recommended meal insulin infusion signal in response to data relating to intake of a meal by the patient, and a compensation control to target controller device configured to compute a recommended residual insulin infusion signal in response to data relating to glucose level excursions of the patient caused by non-meal occurrences; and a supervision controller device configured to receive the insulin infusion signals from the activated controller devices, receive default insulin infusion signals for non-activated controller devices, monitor these insulin infusion signals, and adjust them in accordance with a total insulin infusion amount in dependence on the number of controller devices activated in the modular system, to produce an adjusted total insulin infusion signal, wherein the supervision controller device sends the adjusted total insulin infusion signal to the patient as a suggestion, in an open loop control mode, and sends the adjusted total insulin infusion signal to an insulin infusion pump in a closed loop control mode in order for the insulin infusion pump to administer insulin based on the adjusted total insulin infusion signal, wherein the supervision controller device is distinct and external to each of the daily profile controller device, the meal controller device, and the compensation control to target controller device; and a data acquisition controller device configured to receive continuous glucose monitoring data, insulin pump data, exercise data, and meal data from external data sources, and the data acquisition controller device is configured to output data to the system coordinator controller device, such that the system coordinator controller receives the output data in addition to the received metabolic measurement data and the metabolic state estimate data.

2. The apparatus of claim 1, wherein the data outputted by the data acquisition controller device includes:
a single, processed glucose sample at a specific time, a history of glucose samples up to a specific time, or a statistic computed from glucose samples up to a specific time;
a most recent actual insulin pump command, a history of recent insulin pump commands up to a specific time, or a statistic computed from recent commands;
exercise process data at the specific time; and
meal data at the specific time.

3. The apparatus of claim 2, further comprising at least one observer controller device configured to receive the data outputted by the data acquisition controller device, and to compute said metabolic measurement data and metabolic state estimate data.

4. The apparatus of claim 3, wherein the metabolic measurement data includes at least one of continuous glucose measurements and insulin measurements.

5. The apparatus of claim 4, wherein metabolic state data includes at least one of meal data, exercise data, insulin infusion data, glucagon infusion data, and hypoglycemia treatment data.

6. The apparatus of claim 5, wherein the supervision controller device is configured to receive data from the at least one observer controller device and the controller devices, to determine from the received data whether a predefined increased risk of hypoglycemia or hyperglycemia exists, to reduce or discontinue a suggested insulin infusion if the predefined increased risk of hypoglycemia is determined to exist, and to notify a user if the predefined increased risk of hyperglycemia is determined to exist.

7. The apparatus of claim 3, wherein said at least one observer controller device comprises a short term observer controller device configured to receive data X times per hour, where $0<X\leq7200$, and to output at least one of a vector of estimates of metabolic states of an individual; a single, processed glucose sample at a specific time, a history of glucose samples up to a specific time, or a statistic computed from glucose samples up to a specific time.

8. The apparatus of claim 3, wherein said at least one observer controller device comprises a long term observer controller device configured to assess a patient profile X times per month, where $0<X\leq60$, and to output at least one of a daily profile of an individual's meal behavior as a function of the time of day; a daily profile of the individual's exercise behavior as a function of the time of day; and a daily profile of the individual's utilization of insulin as a function of the time of day.

9. The apparatus of claim 1, wherein the daily profile controller device operates to compute a reference insulin infusion signal once per day; the compensation control to target controller device operates to compute a recommended residual insulin infusion signal every fifteen to thirty minutes; and the meal controller device operates to compute a recommended meal insulin infusion signal every several hours.

10. A system for managing diabetes of a patient, the system comprising:
the apparatus of claim 1 in combination with the insulin infusion pump.

11. A non-transitory computer readable medium, having stored thereon processor-executable instructions that when executed cause a processor to:
receive metabolic measurement data and metabolic state estimate data of a patient and to selectively route this data to a selected number of activated controller devices selectively activated by a system coordinator controller device for particularized diabetes management of a specific patient;
compute a reference insulin infusion signal in response to at least a metabolic state estimate of said patient;
compute a recommended meal insulin infusion signal in response to data relating to intake of a meal by the patient;
compute a recommended residual insulin infusion signal in response to data relating to glucose level excursions of the patient caused by non-meal occurrences;
receive the recommended insulin infusion signals from said computation, monitor these insulin infusion signals, and adjust them in accordance with a total insulin infusion amount in dependence on a number of activated controller devices, to produce an adjusted total insulin infusion signal;
send the adjusted total insulin infusion signal to the patient as a suggestion, in an open loop control mode; and
send the adjusted total insulin infusion signal to an insulin infusion pump in a closed loop control mode in order for the insulin infusion pump to administer insulin based on the adjusted total insulin infusion signal,
wherein instructions cause a processor to receive, via a data acquisition controller device, continuous glucose monitoring data, insulin pump data, exercise data, and meal data from external data sources in addition to the received metabolic measurement data and metabolic state estimate data.

12. The non-transitory computer readable medium of claim 11, further comprising instructions that cause a processor to output data including:
a single, processed glucose sample at a specific time, a history of glucose samples up to a specific time, or a statistic computed from glucose samples up to a specific time;
a most recent actual insulin pump command, a history of recent insulin pump commands up to a specific time, or a statistic computed from recent commands;
exercise process data at the specific time; and
meal data at the specific time.

13. The non-transitory computer readable medium of claim 12, further comprising instructions that cause a processor to receive data outputted by a data acquisition module, and to compute said metabolic measurement data and metabolic state estimate data.

14. The non-transitory computer readable medium of claim 13, wherein the metabolic measurement data includes at least one of continuous glucose measurements and insulin measurements.

15. The non-transitory computer readable medium of claim 14, wherein metabolic state data includes at least one of meal data, exercise data, insulin infusion data, glucagon infusion data, and hypoglycemia treatment data.

16. The non-transitory computer readable medium of claim 15, further comprising instructions that cause a processor to receive data from at least one observer module and control module, to determine from the received data whether a predefined increased risk of hypoglycemia or hyperglycemia exists, to reduce or discontinue a suggested insulin infusion if the predefined increased risk of hypoglycemia is determined to exist, and to notify a user if the predefined increased risk of hyperglycemia is determined to exist.

17. The non-transitory computer readable medium of claim 13, further comprising instructions that cause a processor to receive data X times per hour, where $0 < X \leq 7200$, and to output at least one of a vector of estimates of metabolic states of an individual; a single, processed glucose sample at a specific time, a history of glucose samples up to a specific time, or a statistic computed from glucose samples up to a specific time.

18. The non-transitory computer readable medium of claim 13, further comprising instructions that cause a processor to assess a patient profile X times per month, where $0 < X \leq 60$, and to output at least one of a daily profile of an individual's meal behavior as a function of the time of day; a daily profile of the individual's exercise behavior as a function of the time of day; and a daily profile of the individual's utilization of insulin as a function of the time of day.

* * * * *